(12) United States Patent
Palanker et al.

(10) Patent No.: US 12,290,471 B2
(45) Date of Patent: May 6, 2025

(54) FLUID DELIVERY ALIGNMENT SYSTEM

(71) Applicant: Bausch + Lomb Ireland Limited, Dublin (IE)

(72) Inventors: Daniel V. Palanker, Sunnyvale, CA (US); Yehuda Ivri, Newport Coast, CA (US); Mark S. Blumenkranz, Portola Valley, CA (US); Reynaldo Quintana, Menlo Park, CA (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 287 days.

(21) Appl. No.: 17/670,215

(22) Filed: Feb. 11, 2022

(65) Prior Publication Data

US 2022/0160542 A1     May 26, 2022

Related U.S. Application Data

(63) Continuation of application No. 16/463,137, filed as application No. PCT/US2018/064529 on Dec. 7, 2018, now Pat. No. 11,278,448.

(60) Provisional application No. 62/653,446, filed on Apr. 5, 2018, provisional application No. 62/613,908, filed (Continued)

(51) Int. Cl.
*A61F 9/00* (2006.01)

(52) U.S. Cl.
CPC .................. *A61F 9/0026* (2013.01)

(58) Field of Classification Search
CPC ........ A61F 9/00; A61F 9/0008; A61F 9/0026; A61M 11/005; A61M 15/08; A61M 2205/3313; A61M 2210/0612; B05B 12/122; B05B 17/04

See application file for complete search history.

(56) References Cited

U.S. PATENT DOCUMENTS

| 3,640,274 A | 2/1972 | Costello |
| 3,779,245 A | 12/1973 | Windsor |
| 3,812,854 A | 5/1974 | Michaels et al. |

(Continued)

FOREIGN PATENT DOCUMENTS

| CN | 103118642 A | 5/2013 |
| CN | 104146816 A | 11/2014 |

(Continued)

OTHER PUBLICATIONS

Abidi et al., "Lifilegrast: A Novel Drug for Treatment of Dry Eye Disease", Journal of Pharmacology and Pharmacotherapy, 2016, vol. 7, pp. 194-198.

(Continued)

*Primary Examiner* — Kai H Weng
(74) *Attorney, Agent, or Firm* — Perilla Knox & Hildebrandt LLP; Stephanie Davy-Jow

(57) ABSTRACT

Aspects of the invention include a device for fluid delivery to the ocular surface having a self-alignment system. The fluid delivery device includes a fluid package having a reservoir and one or more apertures, an actuator component configured to eject fluid from the reservoir through the one or more apertures and an image-based self-alignment system configured to align fluid ejected through the one or more apertures with a target location on the eye of a user. Also provided are methods of using the devices in fluid delivery applications, as well as a kit that includes components of the devices.

10 Claims, 12 Drawing Sheets

Related U.S. Application Data on Jan. 5, 2018, provisional application No. 62/596,668, filed on Dec. 8, 2017.

(56) References Cited

U.S. PATENT DOCUMENTS

| | | | |
|---|---|---|---|
| 3,861,386 A | 1/1975 | Harris et al. |
| 3,934,585 A | 1/1976 | Maurice |
| 3,970,250 A | 7/1976 | Drews |
| 3,976,072 A | 8/1976 | Walker |
| 4,159,803 A | 7/1979 | Cameto et al. |
| 4,300,546 A | 11/1981 | Kruber |
| 4,334,531 A | 6/1982 | Reichl et al. |
| 4,338,576 A | 7/1982 | Takahashi et al. |
| 4,344,744 A | 8/1982 | Schuster et al. |
| 4,352,459 A | 10/1982 | Berger et al. |
| 4,465,234 A | 8/1984 | Maehara et al. |
| 4,632,311 A | 12/1986 | Nakane et al. |
| 4,655,393 A | 4/1987 | Berger |
| 4,793,339 A | 12/1988 | Matsumoto et al. |
| 4,850,534 A | 7/1989 | Takahashi et al. |
| 4,882,150 A | 11/1989 | Kaufman |
| 4,952,581 A | 8/1990 | Bito et al. |
| 4,961,345 A | 10/1990 | Tsuruoka et al. |
| 4,976,259 A | 12/1990 | Higson et al. |
| 4,981,625 A | 1/1991 | Rhim et al. |
| 5,025,957 A | 6/1991 | Ranalletta et al. |
| 5,171,306 A | 12/1992 | Vo |
| 5,232,363 A | 8/1993 | Meller |
| 5,368,582 A | 11/1994 | Bertera |
| 5,370,317 A | 12/1994 | Weston |
| 5,487,378 A | 1/1996 | Robertson et al. |
| 5,549,249 A | 8/1996 | Foster et al. |
| 5,624,057 A | 4/1997 | Lifshey |
| 5,627,611 A | 5/1997 | Scheiner |
| 5,630,793 A | 5/1997 | Rowe |
| 5,657,926 A | 8/1997 | Toda |
| 5,692,651 A | 12/1997 | Fuchs |
| 5,811,443 A | 9/1998 | DeSantis, Jr. et al. |
| 5,828,394 A | 10/1998 | Khuri-Yakub et al. |
| 5,938,117 A | 8/1999 | Ivri |
| 5,958,342 A | 9/1999 | Gamble et al. |
| 5,960,224 A | 9/1999 | Sanada et al. |
| 6,024,717 A | 2/2000 | Ball et al. |
| 6,062,212 A | 5/2000 | Davison et al. |
| 6,065,623 A | 5/2000 | Hierzer et al. |
| 6,095,376 A | 8/2000 | Hennemann et al. |
| 6,196,218 B1 | 3/2001 | Voges |
| 6,232,129 B1 | 5/2001 | Wiktor |
| 6,273,092 B1 | 8/2001 | Nolan |
| 6,302,101 B1 | 10/2001 | Py |
| 6,467,476 B1 | 10/2002 | Ivri et al. |
| RE38,077 E | 4/2003 | Cohen et al. |
| 6,543,442 B2 | 4/2003 | Gonda et al. |
| 6,629,646 B1 | 10/2003 | Ivri |
| 6,730,066 B1 | 5/2004 | Bennwik et al. |
| 6,758,837 B2 | 7/2004 | Péclat et al. |
| 6,869,275 B2 | 3/2005 | Dante et al. |
| 7,066,398 B2 | 6/2006 | Borland et al. |
| 7,105,357 B1 | 9/2006 | Kalkum et al. |
| 7,201,732 B2 | 4/2007 | Anderson et al. |
| 7,314,938 B2 | 1/2008 | Shen et al. |
| 7,571,722 B2 | 8/2009 | Wuttke et al. |
| 7,745,460 B2 | 6/2010 | Shen et al. |
| 7,790,743 B2 | 9/2010 | Shen et al. |
| 7,874,467 B2 | 1/2011 | Pardes et al. |
| 7,883,031 B2 | 2/2011 | Collins, Jr. et al. |
| 7,928,122 B2 | 4/2011 | Shen et al. |
| 8,012,136 B2 | 9/2011 | Collins, Jr. et al. |
| 8,048,047 B2 | 11/2011 | Domash |
| 8,056,766 B2 | 11/2011 | Grevin |
| 8,128,606 B2 | 3/2012 | Anderson et al. |
| 8,133,210 B2 | 3/2012 | Al-Abdulla et al. |
| 8,144,399 B2 | 3/2012 | Steenblik et al. |
| 8,168,655 B2 | 5/2012 | Gadek et al. |
| 8,273,307 B2 | 9/2012 | Eickhoff et al. |
| 8,367,701 B2 | 2/2013 | Burnier et al. |
| 8,398,001 B2 | 3/2013 | Borland et al. |
| 8,435,544 B2 | 5/2013 | Mitra et al. |
| 8,544,462 B2 | 10/2013 | Papania et al. |
| 8,545,463 B2 | 10/2013 | Collins, Jr. et al. |
| 8,592,450 B2 | 11/2013 | Acheampong et al. |
| 8,629,111 B2 | 1/2014 | Acheampong et al. |
| 8,633,162 B2 | 1/2014 | Acheampong et al. |
| 8,642,556 B2 | 2/2014 | Acheampong et al. |
| 8,648,048 B2 | 2/2014 | Acheampong et al. |
| 8,684,980 B2 | 4/2014 | Hunter et al. |
| 8,685,930 B2 | 4/2014 | Acheampong et al. |
| 8,722,728 B2 | 5/2014 | Wong et al. |
| 8,733,935 B2 | 5/2014 | Ballou, Jr. et al. |
| 8,863,998 B2 | 10/2014 | Painchaud et al. |
| 8,927,574 B2 | 1/2015 | Burnier |
| 8,927,921 B1 | 1/2015 | Nelms et al. |
| 8,936,021 B2 | 1/2015 | Collins, Jr. |
| 9,039,666 B2 | 5/2015 | Voss et al. |
| 9,068,566 B2 | 6/2015 | Ivri |
| 9,085,553 B2 | 7/2015 | Zeller et al. |
| 9,087,145 B2 | 7/2015 | Ballou, Jr. et al. |
| 9,186,690 B2 | 11/2015 | Scanlon et al. |
| 9,216,174 B2 | 12/2015 | Shen et al. |
| 9,238,532 B2 | 1/2016 | Decock et al. |
| 9,248,191 B2 | 2/2016 | Acheampong et al. |
| 9,353,088 B2 | 5/2016 | Burnier |
| 9,447,077 B2 | 9/2016 | Burnier et al. |
| 9,597,230 B2 | 3/2017 | Haffner et al. |
| 9,676,525 B2 | 6/2017 | Greiner-Perth et al. |
| 9,700,686 B2 | 7/2017 | Gavini et al. |
| 9,801,757 B2 | 10/2017 | Voss et al. |
| 9,808,825 B2 | 11/2017 | Aguilar et al. |
| 9,867,933 B2 | 1/2018 | Pardes et al. |
| 9,890,141 B2 | 2/2018 | Burnier |
| 10,073,949 B2 | 9/2018 | Ballou, Jr. et al. |
| 10,105,720 B2 | 10/2018 | Decock et al. |
| 10,124,000 B2 | 11/2018 | Shen et al. |
| 10,154,923 B2 | 12/2018 | Hunter et al. |
| 10,174,017 B2 | 1/2019 | deLong et al. |
| 10,314,740 B2 | 6/2019 | Kraft |
| 10,624,781 B2 | 4/2020 | Ivri |
| 11,278,448 B2 | 3/2022 | Palanker et al. |
| 2001/0035184 A1 | 11/2001 | Schuler et al. |
| 2001/0036424 A1 | 11/2001 | Takahashi et al. |
| 2001/0036449 A1 | 11/2001 | Garst |
| 2002/0078947 A1 | 6/2002 | Gumaste |
| 2002/0124843 A1 | 9/2002 | Skiba et al. |
| 2002/0158196 A1 | 10/2002 | Berggren et al. |
| 2002/0161344 A1 | 10/2002 | Peclat et al. |
| 2002/0185125 A1 | 12/2002 | Klimowicz et al. |
| 2002/0190079 A1 | 12/2002 | Hamamoto |
| 2003/0052573 A1 | 3/2003 | Wischnewskiy |
| 2003/0065294 A1 | 4/2003 | Pickup et al. |
| 2003/0071071 A1 | 4/2003 | Garcia et al. |
| 2003/0140921 A1 | 7/2003 | Smith et al. |
| 2004/0039355 A1 | 2/2004 | Gonzalez et al. |
| 2004/0050861 A1 | 3/2004 | Lisec et al. |
| 2004/0138630 A1 | 7/2004 | Al-Abdulla et al. |
| 2004/0163645 A1 | 8/2004 | Connelly et al. |
| 2004/0173642 A1 | 9/2004 | Clifford et al. |
| 2004/0204674 A1 | 10/2004 | Anderson et al. |
| 2004/0215157 A1 | 10/2004 | Peclat et al. |
| 2004/0256487 A1 | 12/2004 | Collins, Jr. et al. |
| 2004/0263567 A1 | 12/2004 | Hess et al. |
| 2004/0267214 A1* | 12/2004 | Kerssies ............ A61F 9/0026 604/295 |
| 2005/0001981 A1 | 1/2005 | Anderson et al. |
| 2005/0006417 A1 | 1/2005 | Nicol et al. |
| 2005/0107832 A1 | 5/2005 | Bernabei |
| 2005/0172962 A1 | 8/2005 | Gumaste et al. |
| 2005/0207917 A1 | 9/2005 | Koerner et al. |
| 2005/0240162 A1 | 10/2005 | Chen et al. |
| 2005/0261641 A1 | 11/2005 | Warchol et al. |
| 2006/0065677 A1 | 3/2006 | Py et al. |
| 2006/0069358 A1 | 3/2006 | Gerondale |
| 2006/0147313 A1 | 7/2006 | Zengerle et al. |
| 2006/0210604 A1 | 9/2006 | Dadey et al. |
| 2007/0051362 A1 | 3/2007 | Sullivan et al. |

(56) References Cited

U.S. PATENT DOCUMENTS

| | | |
|---|---|---|
| 2007/0088267 A1 | 4/2007 | Shekalim |
| 2007/0088268 A1 | 4/2007 | Edwards |
| 2007/0102455 A1 | 5/2007 | Stark et al. |
| 2007/0119969 A1 | 5/2007 | Collins et al. |
| 2007/0195151 A1 | 8/2007 | Anderson et al. |
| 2007/0268340 A1 | 11/2007 | Dacquay et al. |
| 2007/0295332 A1 | 12/2007 | Ziegler et al. |
| 2008/0039807 A1 | 2/2008 | Pine |
| 2008/0202514 A1 | 8/2008 | Kriksunov et al. |
| 2008/0214940 A1 | 9/2008 | Benaron et al. |
| 2008/0233053 A1 | 9/2008 | Gross et al. |
| 2008/0247264 A1 | 10/2008 | Gabl et al. |
| 2008/0257911 A1 | 10/2008 | Choi et al. |
| 2009/0060793 A1 | 3/2009 | Eickhoff et al. |
| 2009/0114742 A1 | 5/2009 | Collins, Jr. |
| 2009/0134235 A1 | 5/2009 | Ivri |
| 2009/0182291 A1 | 7/2009 | Eilat |
| 2009/0192443 A1 | 7/2009 | Collins, Jr. |
| 2009/0212127 A1 | 8/2009 | Reynolds et al. |
| 2009/0212133 A1 | 8/2009 | Collins, Jr. |
| 2009/0223513 A1 | 9/2009 | Papania et al. |
| 2010/0001090 A1 | 1/2010 | Neergaard et al. |
| 2010/0005903 A1 | 1/2010 | Beavis |
| 2010/0013352 A1 | 1/2010 | Pletner et al. |
| 2010/0044460 A1 | 2/2010 | Sauzade |
| 2010/0072301 A1 | 3/2010 | Cater |
| 2010/0072302 A1 | 3/2010 | Cater |
| 2010/0076388 A1 | 3/2010 | Cater |
| 2010/0147899 A1 | 6/2010 | Nardi |
| 2010/0186738 A1 | 7/2010 | Kobayashi et al. |
| 2010/0222752 A1 | 9/2010 | Collins, Jr. et al. |
| 2010/0236545 A1 | 9/2010 | Kern |
| 2010/0295420 A1 | 11/2010 | Wierach |
| 2010/0326431 A1 | 12/2010 | Yu |
| 2011/0074247 A1 | 3/2011 | Hohlfeld et al. |
| 2011/0102735 A1 | 5/2011 | Gupta et al. |
| 2011/0106025 A1 | 5/2011 | Hall et al. |
| 2011/0146670 A1 | 6/2011 | Gallem et al. |
| 2011/0284579 A1 | 11/2011 | Pardes et al. |
| 2011/0293452 A1 | 12/2011 | Kim et al. |
| 2011/0305425 A1 | 12/2011 | Fabrykowski et al. |
| 2012/0017898 A1 | 1/2012 | Moller |
| 2012/0062840 A1 | 3/2012 | Ballou, Jr. et al. |
| 2012/0070467 A1 | 3/2012 | Ballou, Jr. et al. |
| 2012/0143152 A1 | 6/2012 | Hunter et al. |
| 2012/0179122 A1 | 7/2012 | Eilat et al. |
| 2012/0197219 A1 | 8/2012 | Scanlon et al. |
| 2012/0304929 A1 | 12/2012 | Ivri |
| 2013/0002095 A1 | 1/2013 | Van der Linden |
| 2013/0017283 A1 | 1/2013 | Zemel et al. |
| 2013/0025038 A1 | 1/2013 | Frey et al. |
| 2013/0053042 A1 | 2/2013 | Tanikawa et al. |
| 2013/0079733 A1 | 3/2013 | Burt et al. |
| 2013/0118619 A1 | 5/2013 | Loth et al. |
| 2013/0140225 A1 | 6/2013 | Decock et al. |
| 2013/0150812 A1 | 6/2013 | Hunter et al. |
| 2013/0152796 A1 | 6/2013 | Pawl |
| 2013/0153677 A1 | 6/2013 | Leen et al. |
| 2013/0164436 A1 | 6/2013 | Yagi et al. |
| 2013/0172830 A1 | 7/2013 | Hunter et al. |
| 2013/0206857 A1 | 8/2013 | Ivri |
| 2013/0299607 A1 | 11/2013 | Wilkerson et al. |
| 2013/0345672 A1 | 12/2013 | Ferreri et al. |
| 2014/0088524 A1 | 3/2014 | Marx |
| 2014/0113946 A1 | 4/2014 | Abad |
| 2014/0157956 A1 | 6/2014 | Date et al. |
| 2014/0171490 A1 | 6/2014 | Gross et al. |
| 2014/0187969 A1* | 7/2014 | Hunter ............... A61B 3/14 604/521 |
| 2014/0214024 A1 | 7/2014 | Eichler |
| 2014/0224267 A1 | 8/2014 | Levitz et al. |
| 2014/0242022 A1 | 8/2014 | Vehige et al. |
| 2014/0249491 A1 | 9/2014 | Ballou, Jr. et al. |
| 2014/0257172 A1 | 9/2014 | Yalamanchili |
| 2014/0274910 A1 | 9/2014 | Cumberlidge et al. |
| 2014/0276054 A1 | 9/2014 | Hossack et al. |
| 2014/0285121 A1 | 9/2014 | Balogh et al. |
| 2014/0323931 A1 | 10/2014 | Avni |
| 2014/0336596 A1 | 11/2014 | Wochele |
| 2014/0336618 A1 | 11/2014 | Wilkerson et al. |
| 2015/0018781 A1 | 1/2015 | Rinderknect et al. |
| 2015/0035180 A1 | 2/2015 | Shen et al. |
| 2015/0036219 A1 | 2/2015 | Shen et al. |
| 2015/0040891 A1 | 2/2015 | Avni |
| 2015/0086397 A1 | 3/2015 | Ma |
| 2015/0097050 A1 | 4/2015 | Ciervo |
| 2015/0139973 A1 | 5/2015 | Steinfeld et al. |
| 2015/0144128 A1 | 5/2015 | Hijlkema et al. |
| 2015/0209174 A1 | 7/2015 | Abreu |
| 2015/0209178 A1 | 7/2015 | Blakey et al. |
| 2015/0238689 A1 | 8/2015 | Shimizu |
| 2015/0256730 A1 | 9/2015 | Shen et al. |
| 2015/0276994 A1 | 10/2015 | Shen et al. |
| 2015/0308421 A1 | 10/2015 | Vogt |
| 2015/0328151 A1 | 11/2015 | Ballou, Jr. et al. |
| 2015/0352297 A1 | 12/2015 | Stedman et al. |
| 2016/0107180 A1 | 4/2016 | Decock et al. |
| 2016/0120833 A1 | 5/2016 | Wan et al. |
| 2016/0129467 A1 | 5/2016 | Ciardella et al. |
| 2016/0199225 A1 | 7/2016 | Ivri |
| 2016/0199230 A1 | 7/2016 | Doshi et al. |
| 2016/0213866 A1 | 7/2016 | Tan |
| 2016/0263314 A1 | 9/2016 | Pardes et al. |
| 2016/0296367 A1 | 10/2016 | Ivri |
| 2016/0354559 A1 | 12/2016 | Gavini et al. |
| 2017/0028626 A1 | 2/2017 | Delrot et al. |
| 2017/0136484 A1 | 5/2017 | Wilkerson et al. |
| 2017/0138357 A1 | 5/2017 | Kondo et al. |
| 2017/0151088 A1 | 6/2017 | Ballou, Jr. et al. |
| 2017/0156927 A1 | 6/2017 | Richter et al. |
| 2017/0182510 A1 | 6/2017 | Wilkerson et al. |
| 2017/0187969 A1 | 6/2017 | Kitamori et al. |
| 2017/0274159 A1 | 9/2017 | Gavini et al. |
| 2017/0344714 A1 | 11/2017 | Ballou, Jr. et al. |
| 2018/0085251 A1 | 3/2018 | Hunter et al. |
| 2018/0108275 A1 | 4/2018 | Newberry et al. |
| 2018/0116871 A1 | 5/2018 | Hunter et al. |
| 2018/0207030 A1 | 7/2018 | Ivri et al. |
| 2018/0229247 A1 | 8/2018 | Laidler |
| 2018/0236466 A1 | 8/2018 | Laidler |
| 2018/0297053 A1 | 10/2018 | Buckland et al. |
| 2019/0053945 A1 | 2/2019 | Hunter et al. |
| 2019/0074086 A1 | 3/2019 | Ballou, Jr. et al. |
| 2019/0099071 A1 | 4/2019 | Ehrmann |
| 2019/0314195 A1 | 10/2019 | Ivri et al. |
| 2019/0314196 A1 | 10/2019 | Ivri et al. |
| 2019/0314197 A1 | 10/2019 | Ivri et al. |
| 2019/0314198 A1 | 10/2019 | Ivri et al. |
| 2020/0022416 A1 | 1/2020 | Alarcon |
| 2020/0197218 A1 | 6/2020 | Newell et al. |
| 2020/0197220 A1 | 6/2020 | Ivri |
| 2020/0246182 A1 | 8/2020 | Ivri |
| 2020/0281768 A1 | 9/2020 | Quintana et al. |
| 2020/0315842 A1 | 10/2020 | Palanker et al. |
| 2020/0330267 A1 | 10/2020 | Li et al. |
| 2021/0128350 A1 | 5/2021 | Ivri et al. |
| 2021/0137732 A1 | 5/2021 | Quintana et al. |
| 2021/0220169 A1 | 7/2021 | Ivri |
| 2021/0322209 A1 | 10/2021 | Ivri |
| 2021/0322210 A1 | 10/2021 | Ivri |
| 2022/0039998 A1 | 2/2022 | Ivri |
| 2022/0125631 A1 | 4/2022 | Ianchulev et al. |
| 2022/0192874 A1 | 6/2022 | Ivri |

FOREIGN PATENT DOCUMENTS

| | | |
|---|---|---|
| CN | 104582647 A | 4/2015 |
| CN | 204813955 U | 12/2015 |
| CN | 105351426 A | 2/2016 |
| CN | 107530509 A | 1/2018 |
| EP | 0622035 A1 | 11/1994 |
| EP | 0622035 B1 | 3/1999 |
| EP | 1493410 A2 | 1/2005 |
| JP | H08251948 A | 9/1996 |

(56) References Cited

FOREIGN PATENT DOCUMENTS

| | | |
|---|---|---|
| JP | 3055480 U | 1/1999 |
| JP | 2007531577 A | 11/2007 |
| JP | 2013535250 A | 9/2013 |
| KR | 10-1258025 B1 | 4/2013 |
| KR | 10-2013-0054352 A | 5/2013 |
| WO | 1994020875 A3 | 1/1995 |
| WO | 1996000050 A1 | 1/1996 |
| WO | 2000005482 A1 | 2/2000 |
| WO | 2001046134 A1 | 6/2001 |
| WO | 2002072169 A2 | 9/2002 |
| WO | 2010078428 A1 | 7/2010 |
| WO | 2012009706 A1 | 1/2012 |
| WO | 2013076682 A1 | 5/2013 |
| WO | 2013090459 A1 | 6/2013 |
| WO | 2013090468 A1 | 6/2013 |
| WO | 2013155201 A2 | 10/2013 |
| WO | 2013158967 A2 | 10/2013 |
| WO | 2016115050 A1 | 7/2016 |
| WO | 2016164830 A1 | 10/2016 |
| WO | 2018136618 A2 | 7/2018 |
| WO | 2018227190 A1 | 12/2018 |
| WO | 2019113483 A1 | 6/2019 |
| WO | 2020010116 A1 | 1/2020 |

OTHER PUBLICATIONS

Ali et al., "Glaucoma and Dry Eye", Ophthalmology, 2009, vol. 116, p. 1232.
Choi et al., "Generation of Controllable Monodispersed Sprays Using Impulse Jet and Charging Techniques", Review of Scientific Instruments, 1990, vol. 61, pp. 1689-1693.
Anchulev et al., "Pharmacodynamic Profile of Mydriatic Agents Delivered by Ocular Piezo-Ejection Microdosing Compared With Conventional Eyedropper", 2016, Ther. Deliv., vol. 7, pp. 751-760.
Jow et al., "Design and Optimization of Printed Spiral Coils for Efficient Transcutaneous Inductive Power Transmission", IEEE Transactions on Biomedical Circuits and Systems, 2007, vol. 1, pp. 193-202.
Kent, Christopher, "Getting Meds onto the Eye, 21st Century Style", Mar. 15, 2013 [online]; [Retrieved on Aug. 27, 2019], Retrieved from the Internet <URL: https://www.reviewofophthalmology.com/article/getting-meds-onto-the-eye-21st-century-style>.
Lallemand et al., "Cyclosporine A Delivery to the Eye: A Comprehensive Review of Academic and Industrial Efforts", European Journal of Pharmaceutics and Biopharmaceutics, 2017, vol. 117, pp. 14-28.
Lindblad et al., "Production of Uniform-Sized Liquid Droplets", Journal of Scientific Instruments, 1965, vol. 42, pp. 635-638.
Lux et al., "A comparative bioavailability study of three conventional eye drops versus a single lyophilisate", Br. J. Ophthalmol., 2003, vol. 87, pp. 436-440.
Macmillan Online Dictionary, "Stream," n.d. [online]; [Retrieved on Dec. 13, 2018]; Retrieved from the Internet <URL: https://macmillandictionary.com/dictionary/american/stream_ 1#stream_ 9>.
Merriam-Webster, "Clamp," 2019 [online]; [Retrieved on Oct. 25, 2022], Retrieved from the Internet <URL: https://www.merriam-webster.com/dictionary/clamp>.
Murube et al., "Classification of Artificial Tears, I: Composition and Properties", Advanced Experimental Medical Biology, 1998, vol. 438, pp. 693-704.
Murube et al., Classification of Artificial Tears, II: Additives and Commercial Formulas, Advanced Experimental Medical Biology, 1998, vol. 438, pp. 705-715.
Oxford Online Dictionary, "Stream," n.d. [online]; [Retrieved on Dec. 13, 2018]; Retrieved from the Internet <URL: https://en.oxforddictionaries.com/definition/us/stream>.
Vocabulary.com, "Stream," n.d. [online]; [Retrieved on Dec. 13, 2018]; Retrieved from the Internet <URL: https://www.dictionary.com/stream>.
International Search Report and Written Opinion dated Feb. 5, 2019 in corresponding International Patent Application No. PCT/US2018/064529 (9 pages).
Birkhoff et al., "New Devices for Dispensing Ophthalmic Treatments May Be the Key to Managing the Life Cycles of Established Products", 2010, Drug Delivery Technology, vol. 10, pp. 16-21.
Brenton, "CRUK/10/30: TRICON8—Sample collection of ovarian cancer tissues and blood for translational research from patients participating in the CR-UK/MRC ICON8 trial", 2015, online abstract.
Denion et al., "A 5-Minute Interval between Two Dilating Eye Drops Increases Their Effect", Jul. 19, 2017, Optometry and Vision Science, vol. 94, pp. 838-844.
Electronic Tutorials, "Linear Solenoid Actuator", 2016 [online]; [Retrieved on Oct. 17, 2022], Retrieved from the Internet [URL: https://www.electronics-tutorials.ws/io/io_6.html].
Elert, Glenn, "Spherical mirrors", The Physics Hypertextbook, 2021 [online]; [Retrieved on Oct. 17, 2022], Retrieved from the Internet [URL: https://physics.info/mirrors/].
Gannon, Megan, "The Best Length for Eyelashes, According to Science", Feb. 24, 2015 [online]; [Retrieved on Oct. 17, 2022], Retrieved from the Internet [URL: https://www.livescience.com/49934-optimal-length-for-eyelashes-discovered.html].
Kompella et al., "ISOPT Clinical Hot Topic Panel Discussion on Ocular Drug Delivery", 2019, J. Ocul. Pharmacol. Ther., vol. 35, pp. 457-465.
Marx et al., "Opthalmic Squeeze Dispenser: Eliminating the Need for Additives in Multidose Preservative-Free Eyecare Formulations", 2017, Drug Development Delivery, vol. 17, pp. 40-44.
Merriam-Webster, "Collimate," 2020 [online]; [Retrieved on Oct. 17, 2022], Retrieved from the Internet [URL: https:// www.merriam-webster.com/dictionary/collimated].
Merriam-Webster, "Stream," n.d. [online]; [Retrieved on Dec. 13, 2018], Retrieved from the Internet [URL: https://www.merriam-webster.com/dictionary/stream].
Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.

* cited by examiner

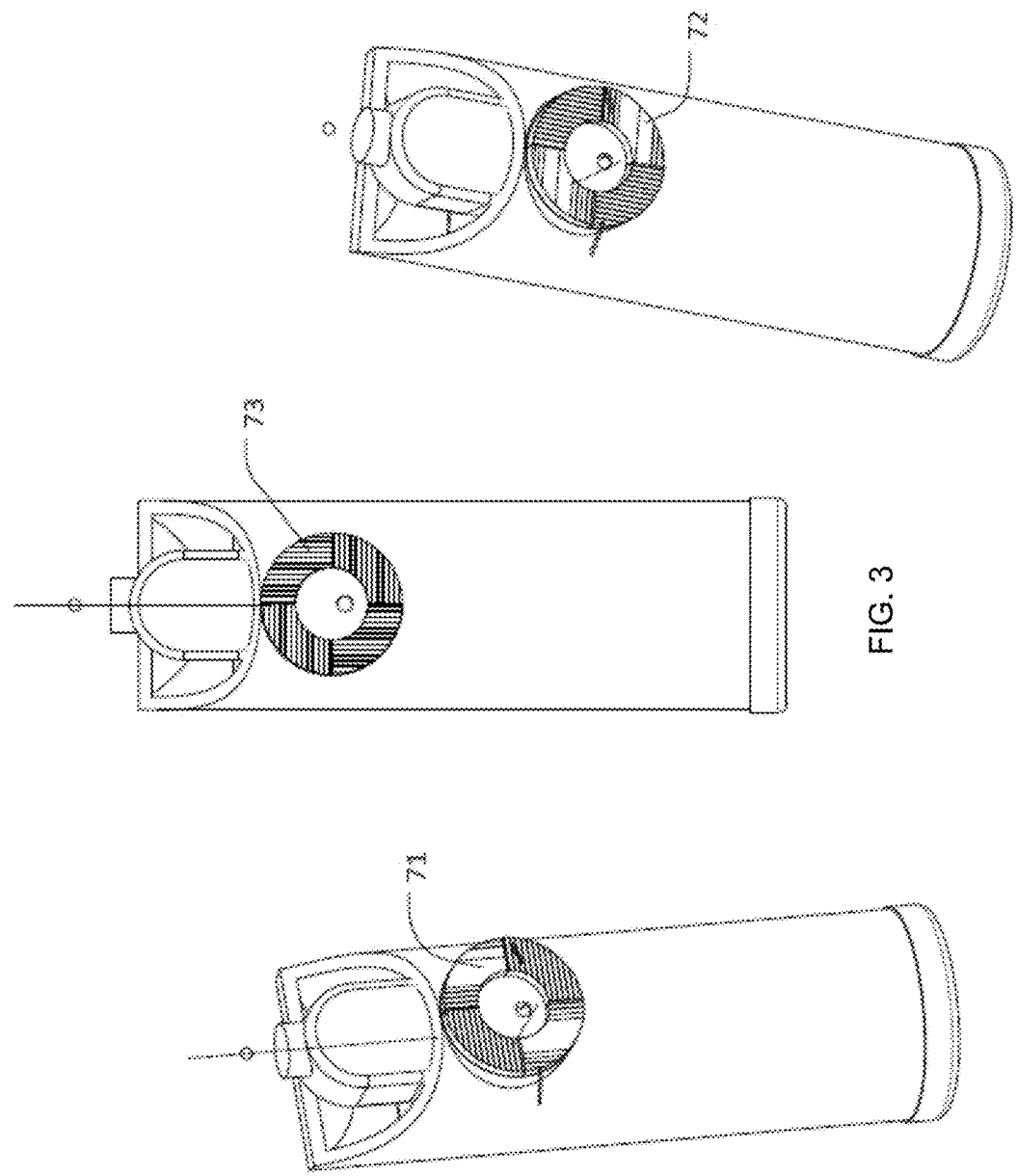

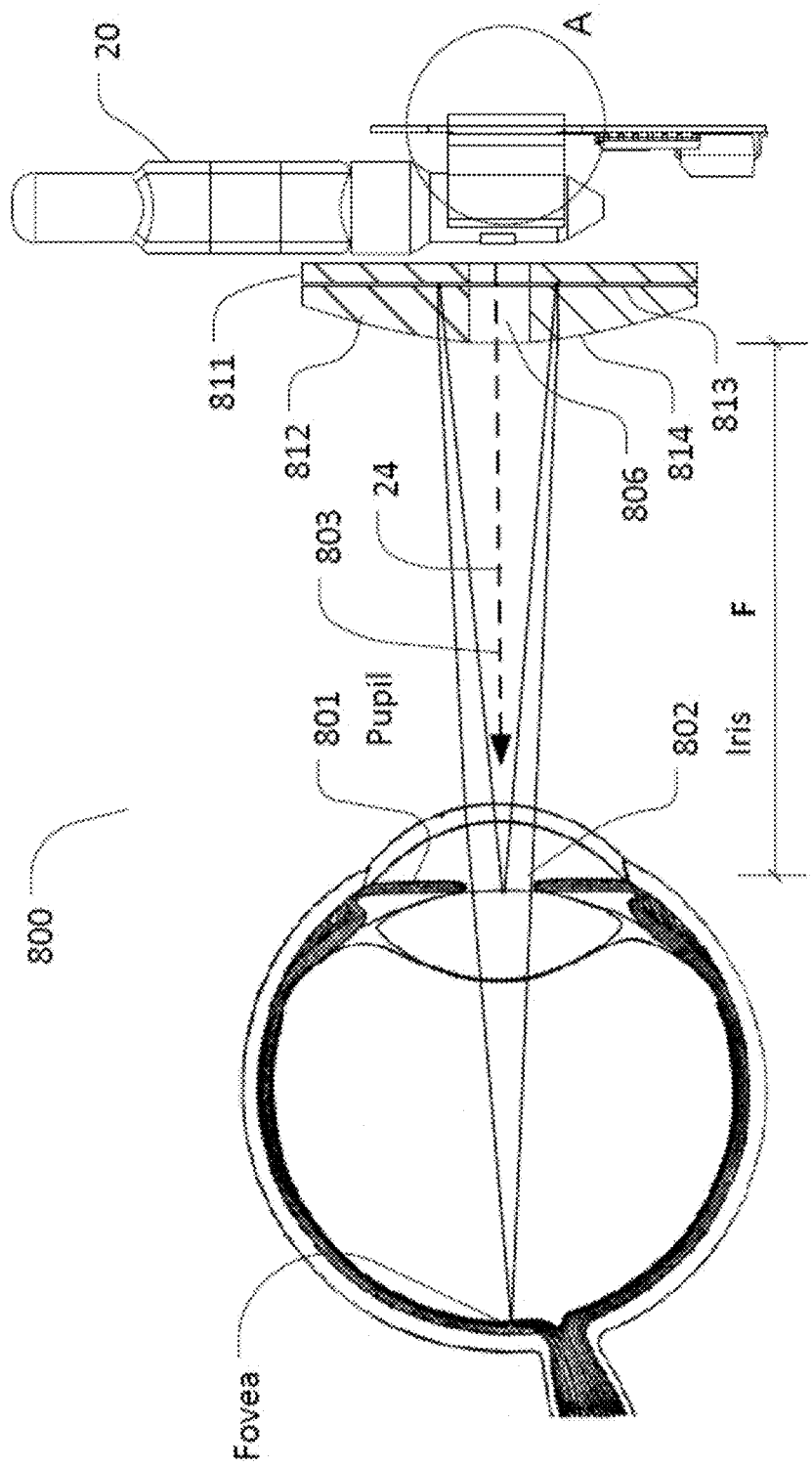

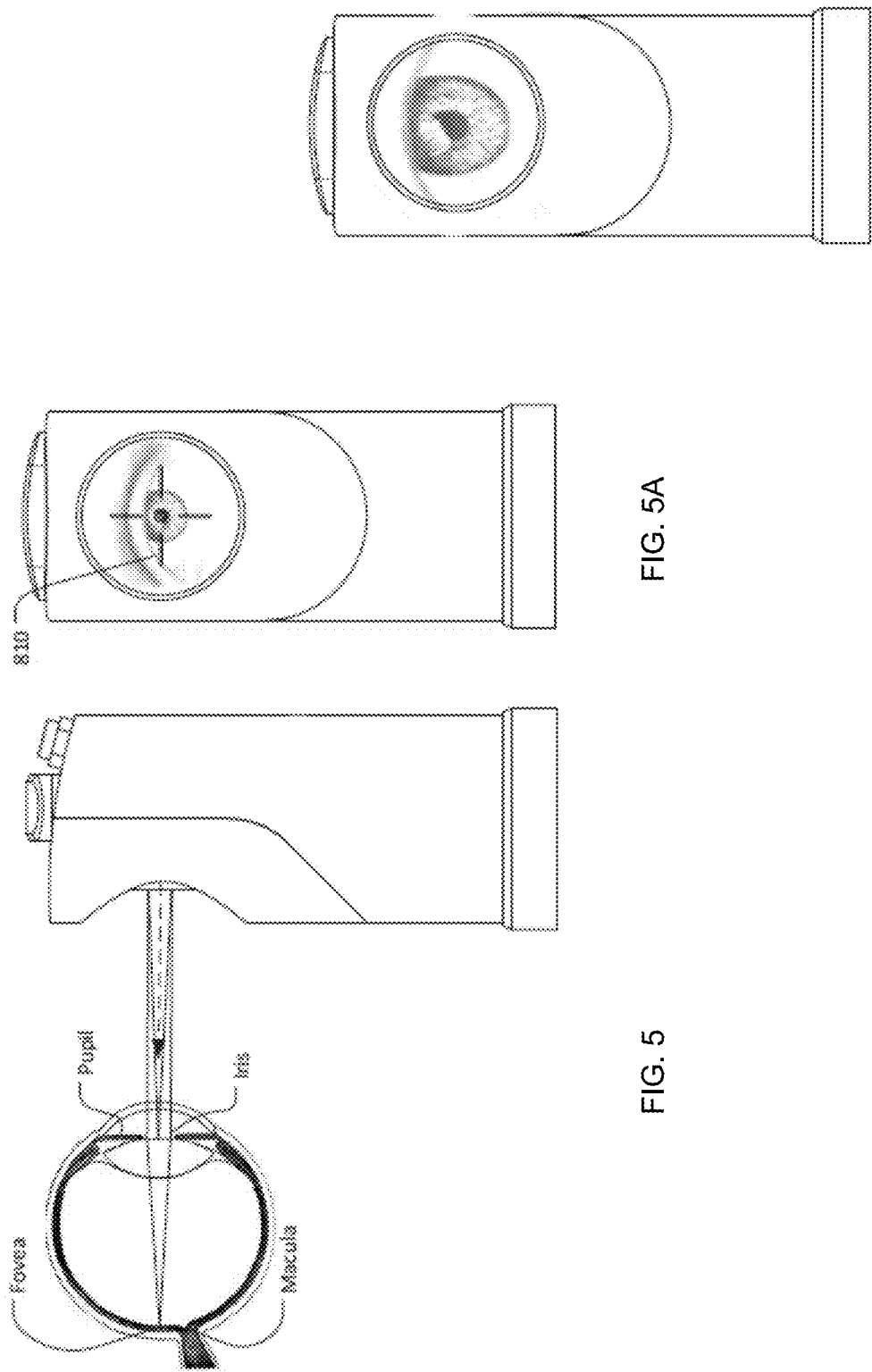

FLUID DELIVERY ALIGNMENT SYSTEM

CROSS-REFERENCE TO RELATED APPLICATIONS

This application is a continuation of U.S. Ser. No. 16/463,137, filed May 22, 2019. Application Ser. No. 16/463,137 is a 371 of PCT/US2018/064529, filed Dec. 7, 2018. Application PCT/US2018/064529 claims the benefit of 62/596,668 filed Dec. 8, 2017, 62/613,908 filed Jan. 5, 2018 and 62/653,446 filed Apr. 5, 2018; the disclosures of which applications are herein incorporated by reference.

INTRODUCTION

A typical medical eye dropper dispenses single drops, typically of about 50 µL in volume. However, since the human eye can typically retain only 7 µL of fluid on the corneal surface, larger deposited volumes result in overflow and loss of most of the medication from the eye surface. In addition, a large volume of a single drop, such as 30 or 50 µL, causes a blinking reflex which removes a majority of the delivered fluid from the cornea as well as discomfort which leads to poor compliance.

U.S. Pat. Nos. 5,630,793 and 8,684,980 (incorporated herein by reference in their entirety) describe a droplet generating device for drug delivery to the eye which comprises a piezoelectric actuated droplet generator for delivering small droplets to the eye. These devices incorporate piezoelectric fluid ejector to dispense droplets to the surface of the eye. Such ejector mechanisms are integrally coupled to a fluid reservoir which may be periodically refilled by the user. Refilling, however, carries the risk of bacterial contamination and the risk of ocular infection. Generally, drug filling, particularly for ophthalmic use, must be processed in tightly controlled aseptic environment which is generally not available to the user.

Another problem associated with the aerosol or jet delivery as described in the prior art is the user ability to direct the aerosol stream to the surface of the eye. Any misalignment of the dispensing device with the eye will result is inaccurate dosing.

SUMMARY

Aspects of the invention include a fluid delivery device having an alignment system, e.g., configured to allow self-administration of fluid delivery by a user to the eye used for visual alignment. The fluid delivery device includes a fluid package having a reservoir and one or more apertures, an actuator configured to eject fluid from the reservoir through the one or more apertures and an image-based alignment system configured to align fluid ejected through the one or more apertures with a target location. In some instances, the image-based alignment system includes a mirror system configured to enable self-alignment of the one or more apertures with the target location by focusing and centering of an image of the eye observed by the same eye of the user in the mirror system. Also provided are methods of using the devices in fluid delivery applications, as well as a kit that include components of the devices.

In some instances, the present invention provides a device for ejecting a fluid to a target location, such as an ocular location, e.g., the cornea or to the conjunctival tissue, of the eye. Embodiments of the device advantageously utilize a drug package, e.g., a disposable sterile drug ampoule which includes a dispensing nozzle, which can be readily attached to and detached from an actuator, such as a piezoelectric transducer, thereby eliminating the need of refilling and mitigating the possibility of bacterial contamination and providing a cost-effective approach by reusing the actuator for further operation. Embodiments of the invention further provide delivery of a liquid stream and a mechanism to align the stream to the target location, e.g., ocular location, prior to actuation to assure convenient and precise dosing. Surprisingly, it has been found that delivery of a single stream causes less discomfort to the eye and is therefore more convenient than delivery of a mist or a distribution of small droplets which have the same total volume. Unlike a mist or spray, a single stream can be precisely oriented to target a specific location, e.g., on the cornea or the conjunctival tissue of the eye. This characteristic is largely attributed to the aerodynamic behavior of the stream. Specifically, delivery of a mist involves turbulence which causes divergence of the droplets from the target while a stream propagates through the air and reaches the target area more precisely.

With respect to embodiments of the invention, fluid delivery alignment systems for ocular applications are described where the device may include a reflective surface having a curved shape which defines a focal plane, wherein the reflective surface may have one or more openings therethrough. The system may also include a fluid delivery assembly configured to emit a fluid from one or more apertures which are aligned with the one or more openings, wherein the system is configured to emit the fluid through the one or more openings and towards the target located in proximity to the focal plane.

BRIEF DESCRIPTION OF THE FIGURES

Having thus summarized the general nature of the invention and some of its features and advantages, certain preferred embodiments and modifications thereof will become apparent to those skilled in the art from the detailed description herein having reference to the figures that follow, of which:

FIG. 1A illustrates a sectional view of piezoelectric clamping actuator and an ampule.

FIG. 3 illustrates the image is produced by the lenticular print when the alignment is correct. FIGS. 3A and 3B illustrate the image that is produced by the lenticular print when the alignment in not correct.

FIG. 4E illustrates another variation of the optical alignment system.

FIGS. 5, 5A and 5B illustrate side and front views of the assembly when the eye of the user is properly positioned relative to the assembly for fluid delivery. FIG. 5B illustrates a front view of the assembly where the radius of curvature of the mirror is relatively smaller than in FIG. 5A such that the image of an eye in reflection appears at higher magnification than in FIG. 5A.

DETAILED DESCRIPTION

Figure 1:
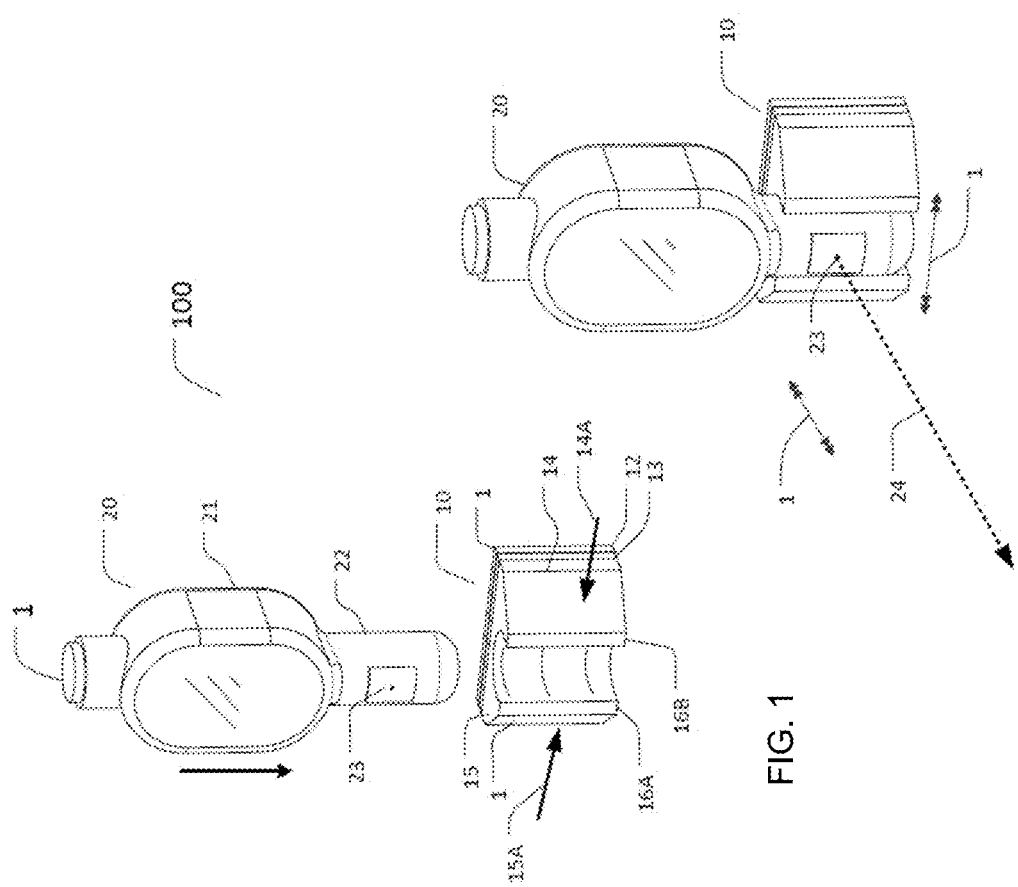
FIG. 1 illustrates perspective exploded view of a piezoelectric clamping actuator and an ampule.

Aspects of the invention include a fluid delivery device having an alignment system, e.g., configured to allow self-administration by a user of fluid to the eye of the user. The fluid delivery device includes a fluid package having a reservoir and one or more apertures, an actuator component configured to eject fluid from the reservoir through the one or more apertures and an image-based alignment system configured to align fluid ejected through the one or more apertures with a target location. In some instances, the image-based alignment system includes a mirror system configured to enable self-alignment of the one or more apertures with the target location by focusing and centering of an image of the eye observed by the same eye of the user in the mirror system. Also provided are methods of using the devices in fluid delivery applications, as well as a kit that include components of the devices.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

As summarized above, fluid delivery devices including an image-based alignment system are provided. In further describing various embodiments of the invention, the fluid delivery devices will be described first in greater detail, followed by a review of various methods of using the devices as well as kits that include the devices or components thereof.

Fluid Delivery Devices

As summarized above, aspects of the invention include fluid delivery devices configured to eject fluid onto a target location of a subject, such as target location of an eye of a subject, i.e., a target ocular location. The fluid delivery devices are, in some instances, configured to provide for self-administration of a fluid by a user to a target location of the user, e.g., a target ocular location. As such, the devices of such embodiments to allow the user to administer a volume of fluid to a target location of the user without any assistance from another individual, such as a health care practitioner.

While the nature of the fluid delivery devices may vary, in some instances the devices are handheld devices. By handheld device is meant that the device is dimensioned and has a weight such that it may be comfortably held by an average adult human hand. In some instances of handheld devices, the device has a longest dimension that is 150 mm or less, such as 125 mm or less, including 100 mm or less, and ranging in some instances from 5 to 100 mm, such as 10 to 100 mm, e.g., from 50 to 100 mm, such as 70 to 85 mm, and a weight that is 150 g or less, such as 125 g or less, including 100 g or less, and in some instances ranging from 10 to 100 g, such as 25 to 100 g, e.g., 40 to 100 g.

The fluid delivery devices described herein may include a fluid package having a reservoir and one or more apertures, an actuator component configured to eject fluid from the reservoir through the one or more apertures and an image-based alignment system configured to align fluid ejected through the one or more apertures with a target location. Additional components may also be present. Each of these components is now reviewed in greater detail.

Fluid Package

The fluid package component of devices of the invention is a fluid container that is configured to hold an amount of fluid and be operably coupled to an actuator, e.g., as described in greater detail below. The container may have any convenient configuration, and may be made of any convenient material, e.g., glass or plastic. The container may be configured to hold a single delivered dosage or multiple deliver delivered dosages, e.g., where the container comprises a volume of the liquid formulation sufficient to provide multiple delivered dosages. As such, the volume of liquid formulation that the container is configured to hold may vary, ranging in some instances from 100 µl to 10 ml, such as 100 to 2000 µl, including 120 to 800 µl. The container includes a reservoir component configured to hold an amount of a fluid, e.g., as described above, and one or more apertures through which fluid from the reservoir component may be ejected during use. While the number of apertures that a given fluid package has may vary, in some instances the number of apertures ranges from 1 to 20, such as 1 to 10, including 1 to 5, e.g., 1 to 4, 1 to 3, and 1 to 2. In some instances, the fluid package includes a single aperture. In some instances, the fluid package includes more than one aperture. The dimensions of a given aperture may vary, as desired. In some instances, the apertures have a longest dimension, e.g., diameter, ranging from 10 to 500µ, such as 50 to 450µ, e.g., 75 to 350µ, where in some instances the apertures have a diameter ranging from 80 to 120µ (such as 80 to 100µ), or 150 to 350µ (such as 200 to 350µ, e.g., 250 to 300µ). While the container may have any convenient configuration, in some instances the container includes a bulb portion that includes the reservoir and a neck portion, e.g., that is configured to operably couple to an actuator and includes the one or more apertures. The fluid package is, in some instances, configured to be disposable. Fluid packages finding use in embodiments of the invention are further described in international application serial no. PCT/US2018/014211 published as WO 2018/136618, the disclosure of which is herein incorporated by reference.

The fluid present in the fluid package may vary, as desired. In some instances, the fluid present in the fluid delivery package is a liquid formulation of an active agent. The terms "agent," "compound," and "drug" are used interchangeably herein to refer to a molecule or molecular combination that has a physiological effect upon contact with a subject via administration to the target topical location of the subject. Examples of active agents that may present in the liquid formulation include, but are not limited to: anti-infectives (including but not limited to antibiotics, antivirals, etc.), anti-inflammatories (including but not limited to steroids and non-steroidal anti-inflammatory drugs (NSAIDS), etc.), anti-allergy agents (including but not limited to anti-histamines and mast cell stabilizers, etc.), anti-fungals, vasoconstrictors, biologics (e.g. proteins, engineered proteins, etc.), small molecules, anesthetics, analgesics, intraocular pressure lowering agents (including but not limited to prostaglandin analogs, ROK inhibitors, beta blockers, carbonic anhydrase inhibitors, and alpha agonists, etc.), lubricants (including but not limited to saline, polymer solutions, proteoglycans, glycosaminoglycans, carbohydrates, etc.), mydriatic (pupil dilating) agents, miotic agents (pupil constricting agents), iodine derivatives, etc.; and/or various combinations thereof. Additional drugs and agents which may be utilized with the devices described may include any number of the agents disclosed in further detail in U.S. Pub. 2017/0344714 and U.S. Pat. No. 9,087,145 the disclosures of which are herein incorporated by reference.

In some embodiments, the concentration of active agent in the liquid formulation ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In addition, the active agent, the liquid formulation may include an aqueous delivery vehicle, e.g., a pharmaceutically acceptable aqueous vehicle. In addition to water the aqueous delivery vehicle may include a number of different components, including but not limited to: salts, buffers, preservatives, solubility enhancers, viscosity modulators, colorants, etc. Suitable aqueous vehicles include sterile distilled or purified water, isotonic solutions such as isotonic sodium chloride or boric acid solutions, phosphate buffered saline (PBS), propylene glycol and butylene glycol. Other suitable vehicular constituents include phenylmercuric nitrate, sodium sulfate, sodium sulfite, sodium phosphate and monosodium phosphate. Additional examples of other suitable vehicle ingredients include alcohols, fats and oils, polymers, surfactants, fatty acids, silicone oils, humectants, moisturizers, viscosity modifiers, emulsifiers and stabilizers. The compositions may also contain auxiliary substances, i.e. antimicrobial agents such as chlorobutanol, parabans or organic mercurial compounds; pH adjusting agents such as sodium hydroxide, hydrochloric acid or sulfuric acid; and viscosity increasing agents such as methylcellulose. An exemplary final composition is sterile, essentially free of foreign particles, and has a pH that allows for patient comfort and acceptability balanced with a pH that is desirable for optimum drug stability. An exemplary "pharmaceutically acceptable vehicle is an "ophthalmically acceptable vehicle" as used herein refers to any substance or combination of substances which are non-reactive with the compounds and suitable for administration to patient. In an exemplary embodiment, the vehicle is an aqueous vehicle suitable for topical application to the patient's eyes. In various embodiments, the vehicle further includes other ingredients which may be desirable to use in the ophthalmic compositions of the present invention include antimicrobials, preservatives, co-solvents, surfactants and viscosity building agents.

Actuator

In addition to the fluid package, the device further includes an actuator component configured to operably couple to the fluid package and eject fluid from the reservoir of the fluid package through the one or more apertures to the target location. In some instances, the actuator is a component that is configured to impart vibration to the contents of the container, where the oscillation frequency of the vibration may vary. In some instances, the oscillation frequency is an ultrasonic frequency, ranging in some instances from 10 to 1000 KHz, such as 20 to 800 KHz, and including 20 to 35 KHz.

The oscillations, e.g., of ultrasonic frequency (such as described above) imparted by the actuator on the fluid package, and in some instances the outer surface of the fluid package, produces cycles of acoustic pressure in the fluid held by the fluid package, resulting in ejection of fluid from the one or more apertures. In some instances, the fluid is ejected from the fluid package by the actuator as a stream, where the stream may be a continuous stream of liquid (i.e., a stream that is not made up of individual droplets) or a discontinuous stream of liquid, e.g., a collimated stream of individual droplets. Where the stream is a continuous stream of liquid, the stream diameter may vary, and in some instances ranges from 0.05 to 0.3 mm, such as from 0.05 to 0.2 mm, including 0.05 to 0.15 mm, such as 0.070 to 0.130 mm. Where the stream is a discontinuous stream of individual droplets, the volume of the individual droplets may vary, ranging in some instances from 50 to 1500 μl, such as 100 to 1000 μl. In some instances, the width of the stream, which may be continuous, discontinuous, or have a component that is continuous and a component that is discontinuous, may by substantially constant along the length of the stream, such that any variation in the width of the stream from the one or more apertures to the target location varies by 5% or less, such as 2% or less. The duration of stream delivery during a given administration event may vary and is selected so as to provide the desired delivered dosage volume. In some instances, the duration of stream delivery, i.e., the duration of administration, ranges from 10 to 3000 msec, such as 100 to 2000 msec, such as 250 to 1000 msec, including 400 to 600 msec.

While the nature of the actuator component may vary, in some instances the actuator component is a piezoelectric actuator, e.g., as described in international application serial nos.: PCTUS2016/012903 published as WO 2016/115050; PCT/US2016/026795 published as WO 2016/164830; and PCT/US2018/014211 published as WO 2018/136618; the disclosure of which is herein incorporated by reference. In some instances, the actuator is an electromagnetic actuator, e.g., as described in U.S. Provisional Application Ser. No. 62/693,818; the disclosure of which is herein incorporated by reference.

Alignment System

As summarized above, embodiments of the fluid delivery devices described herein also include an image-based alignment system configured to align fluid ejected through the one or more apertures of the fluid package with a target location, such as a target ocular location (e.g., as described in greater detail below). The alignment systems are systems that allow user, such as the subject to which the fluid is to be administered, to align the one or more apertures with the target location such that the ejected fluid is delivered to the target location upon actuation of the device. The alignment system is, in some instances, configured so that a user may self-administer the fluid from the device following alignment by the user of the device, e.g., by a protocol described in greater detail below.

As summarized above, the alignment systems are image-based alignment systems. By "image-based" alignment system is meant that alignment of a delivery device with a target location includes visualization of an image, e.g., a picture or a reflection, by a user, e.g., the subject to which fluid is delivered during a self-administration protocol.

Lenticular Print Image-Based Alignment System

In some instances, the image-based alignment system is a system that includes one or more lenticular prints. A lenticular print may include one or more printed images and an array of linear lenses or focusing elements which are overlaying the images. Due to the optical characteristic of the lenses or focusing elements, a portion of the printed image is forms desirable synthetic visible image only from a certain angle. In one embodiment, the fluid delivery device and the lenticular print are positioned such that when the image is visible to the user the stream from the delivery device will reach the target location, such as the surface of the eye. The alignment system may include lenticular prints wherein one pair of linear lenses is perpendicularly positioned relative to a second pair of linear lenses. In this way rotational or angular alignment is achieved with respect to the two axes that are perpendicular to the line of sight or the optical axis of the eye.

In one embodiment, the alignment system includes two pairs of lenticular prints. One pair of prints has an array of vertical linear lenses and a second pair of prints has an array of horizontal linear lenses. The prints of the vertical pair are placed a predetermined distance from each other and the prints in the horizontal pair are positioned a predetermined distance from each other. In this way the desired image is visible to the user only from a certain distance and only in one orientation. The dispensing device and the lenticular prints may be in a position in placement relationship to each such that when the desired image is visible to the user the stream that emits from the dispensing device reaches the target location, e.g., target ocular location. In some instances, the desired image is visible when the delivery device is placed about 50 to 100 mm from the target location. In one alternative embodiment the lens or focusing element comprising an array of lenses or a focusing element and an image-forming system that includes or is formed from an array or pattern designed to collectively form an image or a certain desired pattern only from a predetermined distance and orientation relative to the one or more orifices.

Any convenient lenticular system such as described above may be employed, where examples of such lenticular systems include, but are not limited to, those described in U.S. Pat. Nos. 6,065,623 8,144,399, as well as international patent publication no. WO1994020875; the disclosures of which are herein incorporated by reference. Systems of lens arrays are described in published United States Patent Publication Nos. 2015/0276994, 2015/0256730, 2015/0036219 and 2015/0035180, the disclosures of which are herein incorporated by reference.

Reflective Surface Image-Based Alignment System

Another type of image-based alignment system that may be present in fluid delivery devices of the invention is a reflective surface (i.e., mirror) image-based alignment system, where such systems include one or more reflective surfaces or mirrors, and in some instances include a single reflective surface or mirror. In some instances, the reflective surface has a curved shape which defines a focal point, i.e. comprising a concave mirror.

Typically, the most visible parts of the eye, when looking in a mirror, are the iris, conjunctiva, sclera (through the conjunctiva), and cornea. Ocular tissue in the focal plane of the concave spherical mirror will appear in focus when the mirror is placed at the focal distance (F) from that tissue. The focal point (P) is the intersection of the focal plane with the optical axis of the mirror. One method for delivering fluid to a targeted region may generally comprise positioning a reflective surface having a curved shape into proximity with the targeted region located upon a surface of an eye until a reflection of the eye in the reflective surface appears focused to a subject, wherein a focal plane defined by the reflective surface is coincident with the eye when the reflection appears focused. Once positioned, the method may include actuating a fluid delivery assembly to emit a fluid from one or more apertures so that fluid is delivered to the target location on the eye.

In some instances, the reflective surface defines one or more openings therethrough. In such systems, the system may also include a fluid delivery assembly configured to emit a fluid from one or more apertures which are aligned with the one or more openings, wherein the system is configured to emit the fluid through the one or more openings and towards or in proximity to the focal point. In some instances, the fluid delivery assembly is configured to emit a fluid from one or more apertures which are aligned with one or more openings defined through the reflective surface such that the fluid is directed towards or in proximity to the focal plane and upon the targeted region. In another variation, a system for aligning a fluid delivery assembly relative to a targeted region on an eye of a subject may generally comprise a concave mirror having a reflective surface, wherein the mirror defines a focal plane and one or more openings through the mirror for fluid delivery, and a fluid delivery assembly configured to emit a fluid from one or more apertures which are aligned with the one or more openings such that the fluid is ejected through the one or more openings and towards or in proximity to the focal plane.

Instead of a concave mirror, the reflective imaging assembly may include a flat mirror coupled with a suitable lens that provides for alignment by a user, e.g., as described above and in greater detail below.

Whether the reflective surface is curved or flat, the alignment system may be configured such that in self-administration protocols where the target location is an ocular surface, the user may focus an image of the eye that includes the target location when aligning the fluid delivery device. As such, the same eye that includes the target ocular location is employed by the user to align the fluid delivery device, e.g., by focusing and centering the eye in the mirror of the alignment system.

The dimensions of the reflective surface of such image-based alignment systems may vary, as desired. In some instances, reflective surface has a longest dimension, e.g., diameter, that ranges from 10 to 30 mm. In some instances, the dimensions are such that a subject does not view the entire eye that includes the target ocular location in the mirror. In such instances, the longest dimension, e.g., diameter, may range from 10 to 15 mm, such as 10 mm, 11 mm, 12 mm, 13 mm, 14 mm or 15 mm.

Housing

In some embodiments, the fluid delivery devices include a housing with which the various components of the device, e.g., as described above, are associated. The housing may have any convenient configuration, and in some instances has a longest dimension ranging from 50 to 100 mm, such as 70 to 85 mm. The housing may have any convenient shape, where shapes of interest include those that allow for ready handling and use of the device. In some instances, housing has an approximately rectangular cuboid shape. The housing may be fabricated from any convenient material, such as a plastic or metal material.

While the various components of the device may be associated with the housing component in any convenient manner, in some instances the fluid package and actuator components are present inside the housing, and least a portion of the image-based alignment system is associated with a surface of the housing, e.g., so that the image-based alignment system may be viewed by a user during use.

In some instances, the housing includes a movable cover, e.g., which covers the apertures and/or alignment system when the device is not in use. The cover may be configured to move between closed and open positions, where upon moving the cover from the closed to the open position, the device is transitioned to a configuration where it may be employed to deliver fluid. In some instances, movement of the cover from the closed to the open position may result in the device transitioning from an inactive to active state. For example, movement of the cover from the closed to the open position may results in activation of the actuator component.

Illumination Source

In some instances, the device includes one or more illumination sources. Any convenient illumination source may be employed, where such sources include, but are not limited to, light emitting diodes (LEDs), and the like. When present, the illumination source may take a variety of different configurations. For example, it may be distinct from any other component of the device, such as the alignment system. Alternatively, it may be associated with another component of the device. For example, it may be associated with the alignment system of the device, such as at least partially bounding, if not completely bounding the alignment system of the device. When present, the illumination source may serve a variety of different functions, such as illuminating the target location in a reflective surface of the alignment system, indicating that the device is aligned with the target location, indicating that the device is within a predetermined distance of the target location, indicated that the device is ready to deliver fluid, indicating the amount of fluid in the fluid package (e.g., full, partially full, empty), and the like.

Distance Sensor

In some instances, the device includes one or more distance sensors. A distance sensor is a component configured to determine the distance between the device and the target location. Any convenient distance sensor may be present, where such sensors include, but are not limited to, infra-red (IR) sensors, radar sensors, and the like. In some instances where the device includes a distance sensor, the device may further be configured to provide a signal, such as an auditory or visual signal, when the determined distance between the device and the target location is within a predetermined range. For example, the device may be configured to activate an illumination source, e.g., as described above, when the device is within a predetermined range of the target location as determined by the distance sensor. In some instances, the device is configured to be activated when the determined distance between the device and the target location is within a predetermined range. In the above embodiments, the predetermined range may vary, and in some instances is between 1 mm and 250 mm, such as 10 mm to 100 mm.

Specific Embodiments

One embodiment of a fluid delivery device of the invention is illustrated in FIGS. 1 and 1A, which illustrate a piezoelectric fluid ejection device configured to dispense the content of a fluid-filled ampule directly from the ampule.

The device illustrated in FIGS. 1 and 1A eliminates the need to transfer the contents of the ampule to a secondary dispensing device and the need to sterilize the dispensing device prior to fluid filling. The device is particularly useful for delivery of ophthalmic solution to the surface of the eye (or in some instances the delivery of inhalable solution in a form of fine aerosol). The device comprises a piezoelectric clamping actuator and separable disposable fluid filled ampule. The ampule comprises a thin-walled thermoplastic package which includes a bulb section and a neck section. One or more apertures are positioned on the wall of the neck section of the ampule. The piezoelectric clamping actuator is configured to clamp the circumference of the neck section adjacent to the aperture while and at the same time apply cycles of oscillations in the clamping direction. The oscillations, typically in ultrasonic frequency, produce cycles of acoustic pressure in the fluid resulting in ejection of fluid droplets or streams from the apertures. The fluid-filled ampule may be held vertically while fluid is ejected horizontally, e.g., in a continuous stream, a discontinuous stream of droplets or a combination thereof. In this way fluid is continuously fed from bulb section to the neck section of the ampule neck while fluid is ejected horizontally from the aperture. This orientation is particularly useful for delivery to the surface of the eye and for delivery of inhalable aerosol. Advantageously fluid is ejected directly from the ampule without having to transfer the fluid content to a container, a step that normally requires sterilization of the container.

The ampule can be easily coupled or decoupled from the piezoelectric clamp actuator. Empty drug or fluid packages are disposed, thereby eliminating the need for filling the drug by the user and the risk of bacterial contamination. The fluid package may be coupled to the clamp by a friction fit which generally requires an insertion force that is less than 10 Newton.

The drug or fluid package is configured to dispense micro-droplets by one or more oscillations exerted by the piezoelectric actuator clamp onto the external surface or the neck of the disposable drug package. The drug package can be decoupled from the piezoelectric actuator allowing disposal of used packages while the piezoelectric clamping transducer is subsequently reused with another drug or fluid package. The invention provides cost effective approach for topical drug delivery to the eye.

The piezoelectric clamping actuator is a small module which can be used in a handheld device or as an attachment to an eyewear article such as optical or sunglasses. In one embodiment the fluid ejection device comprises a piezoelectric clamp configured to oscillate at ultrasonic frequency and further includes an ampoule containing a fluid to be dispensed. Ultrasonic oscillations which are generated by the clamp actuator transmitted to the neck of the ampoule and produce cycles of acoustic pressure in the fluid and ejection of droplets from an aperture in the ampoule.

The piezoelectric transducer includes a clamp having two jaws which are structurally connected to a bending actuator. The bending actuator comprising of a laminate two active piezo-ceramic plate oriented in opposite polarity. Such bending actuator is generally known as bimorph actuator oscillates in a bending mode which causing the clamp to cyclically open and close against the neck of the ampule. In one embodiment, the bending actuator comprises a laminate of two active piezo-ceramic plate and one passive plate-in between the two piezo-ceramic plates. For example, the passive layer is a printed circuit board made of FR-4 material. The printed circuit board (PCB) may include all the electronic circuit for driving and controlling the piezo-ceramic clamp. The piezo plates may be attached PCB by solder reflow process. The electrical connection to the piezo plate is made via a cupper pad on the PCB.

The fluid drug package or ampule is made of a thermoplastic polymer such as terephthalate, polyethylene or polypropylene, either high density or low density. The drug or fluid package or ampoule includes a drug reservoir and one or more apertures.

Droplet volumes are generally between, e.g., 100 to 1000 pL, and the size of the aperture is typically between, e.g., 10 to 100 micron. Present in the ampule is an ophthalmic composition. U.S. Pat. Pub. 2012/0070467 (the entirety of which is hereby incorporated by reference herein and for any purpose) describes examples of various ophthalmic compositions and therapeutics which may be used with the devices and methods described herein.

A typical volume of, e.g., between 1 and 10 µL, should be delivered within the blink response time—150 ms, and, if necessary, maybe extended up to 250 ms. In one embodiment the dispensing device includes one or more apertures but typically less than, e.g., 20 apertures, and preferably less than, e.g., 10 apertures and most preferably a single aperture. The apertures are positioned in a predetermined offset relative to the optical axis of the alignment tube. This offset determines where the fluid stream is deposited relative to optical axis of the eye or relative to the center of the pupil or the center of the iris. Typically, the offset may be, e.g., 2-20 mm, from the center of the pupil in the vertical or horizontal directions, or in both vertical and horizontal directions.

The drug or fluid package can be removed and replaced, while the piezoelectric clamp actuator can be reused with another drug package. In one embodiment the drug or fluid package is manufactured by an aseptic blow-fill-seal process commonly used in packaging of pharmaceutical liquids, e.g., as described in international application no. PCT/US2018/014211 published as WO 2018/136618, the disclosure of which is herein incorporated by reference.

The device illustrated in FIGS. 1 and 1A further includes an electronic circuit that is configured to generate and transmit an electric pulse or wave form to the piezoelectric actuator. The circuit may be comprised of a half-bridge driver which generally includes a half-bridge driver chip and two MOSFET transistors. The half-bridge driver receives an input signal and transmits a switching output which drives a pair of MOSFET transistors sequentially "on" and "off". In this way it translates the low voltage input signal to a high power electrical pulse that is capable of driving the piezoelectric actuator. The circuit may further include an inductor which boost the input voltage to the piezoelectric actuator. Preferably the inductance of the inductor and the capacitance of the piezoelectric actuator may be tuned to operate in electrical resonance at the selected frequency. The input signal which transmitted to the half bridge driver chip may be generated by a microprocessor or by a signal generator IC (integrated circuit). In one embodiment the driver, the transistors and the microprocessor are fabricated on a single integrated circuit. Preferably such IC is attached and encapsulated directly to a printed circuit board (PCB) utilizing a chip-on-board (COB) packaging process. In the field of microelectronics COB is used to reduce the size of the circuit. The input voltage of the circuit is preferably below, e.g., 5 volts, and more preferably below, e.g., 3 volts, and even more preferably below, e.g., 1.5 volts. The source of energy may be provided by a power supply such as capacitors, batteries, etc. which may be optionally rechargeable.

When the circuit is driven sequentially "on" and "off" as described earlier the fluid stream emits from the aperture as individual droplets. However, when an inductor is added and is tuned to operate at the electrical resonance of the circuit then the electrical output becomes sinusoidal and the fluid emits as a collimated and continuous stream without individual droplets.

With respect to the device illustrated in FIGS. 1 and 1A, the dispensing device advantageously utilizes a disposable, removable or separable drug or fluid package while desirably retaining the piezoelectric actuator or transducer for subsequent further uses, thereby providing an economical and cost-effective approach with reuse of the piezoelectric actuator or transducer for further operation.

Turning now to FIGS. 1 and 1A, these figures illustrate a prospective view and an exploded prospective view of dispensing device (100) as generally described above. Device (100) comprises a piezoelectric clamping actuator (10) and separable disposable fluid-filled ampule (20). Ampule (20) comprises a thin-walled thermoplastic package which includes a bulb section (21) and a neck section (22). Neck section (22) has a cylindrical shape with a circular cross-sectional shape. Other cross-sectional shapes, such as oval shape, are also possible. One or more apertures (23) are positioned on the wall of the neck section. Piezoelectric clamping actuator (10) is configured to clamp the circumference of the neck section (22) adjacent to the aperture (23) while at the same time apply cycles of oscillations in the clamping direction against the wall of the ampule as illustrated by the arrows (14A) and (15A). Oscillation of ampule neck (20) cyclically deforms the circular shape of the neck section into elliptical shape and produce cycles of acoustic pressure in the fluid within the neck (22) and ejection of droplets (24) from an aperture (23). In an embodiment, the neck of the ampule (22) is inserted into the piezoelectric clamping actuator (10) by light force, typically less than 10 newtons. Once inserted, the cylindrical neck (22) is engaged in an interference fit with the clamp (10) which facilitates transmission of the oscillation amplitude to the ampule neck. Generally, the oscillation amplitude is less than 2 microns.

Figure 2:
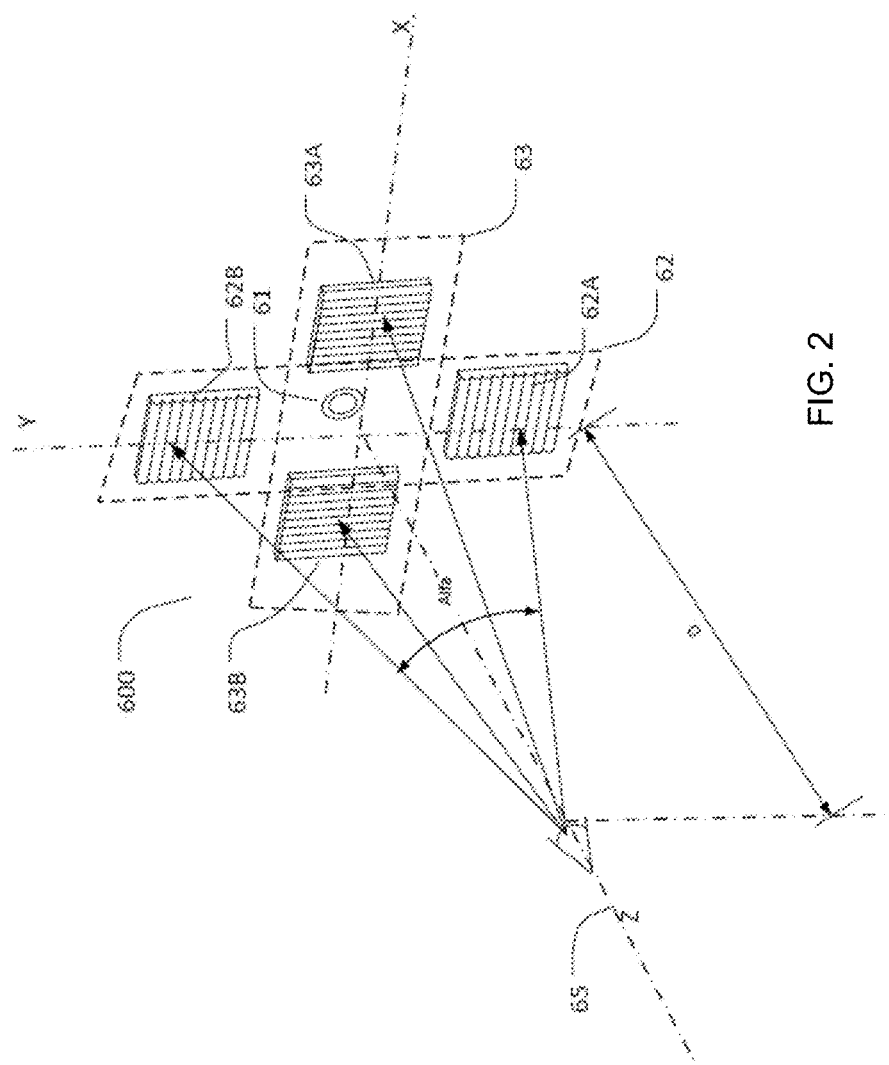
FIG. 2 illustrates a lenticular print system that is use to align the device to the eye.

FIG. 2 illustrates an optical system (600) which aligns or targets the dispensing aperture (61) to the ocular surface or to the area of the lower conjunctiva prior to actuation. Such alignment assures that the entire dose reaches the surface of the eye. The system includes two pairs of lenticular prints, where the first pair (62A) and (62B) are bounded by the dashed lines frame (62) and the second pair (63A) and (63B) are bounded by dashed line frame (63). Lenticular prints are placed on the dispensing device in a predetermined distance from the dispensing aperture (61). The lenticular prints include printed images and an array of linear lenses or focusing elements overlaying the images. Due to the optical characteristic of the lens, a portion of the printed image forms a desirable synthetic image which is visible only from a certain angle. The dispensing device and the lenticular print are positioned such that when the image is visible to the user the stream that emits from the dispensing nozzle (61) reaches the surface of the eye. The alignment system includes a first pair of lenticular prints (62A) and (62B) which includes vertical lenses and a second pair of lenticular prints (63A) and (63B) which includes horizontal lenses. In this way rotational alignment is achieved in the two axes that are perpendicular to the line of sight or the optical axis of the eye (65). Lenticular prints (62) and (63) are visible based upon the correct orientation of the print relative to the eye and also based on the distance from eye since the distance (D) from the eye is a function of the viewing angle (alfa). In this way, the device will be positioned in the desirable distance and orientation relative to the eye of the user, and may be used by the user to align the device for self-administration, e.g., by looking for the proper image from the eye that includes the targe ocular location.

FIGS. 3, 3A and 3B illustrate how the image of the lenticular print may change based on the orientation of the device and its distance relative to the eye that includes the target location. Referring to FIGS. 3A and 3B, when the device is not aligned to the eye or not placed at the right distance from the eye, only a partial image is visible by the eye, typically with voids such as (71) and (72). In contrast, when the dispensing device is properly aligned and at the right distance from the eye, the image (73) appears complete to the eye. Image (73) may be of solid color such as red color or an image that include an intuitive meaning that would indicated a correct alignment such as a "smiley face" or the like.

Figure 4A:
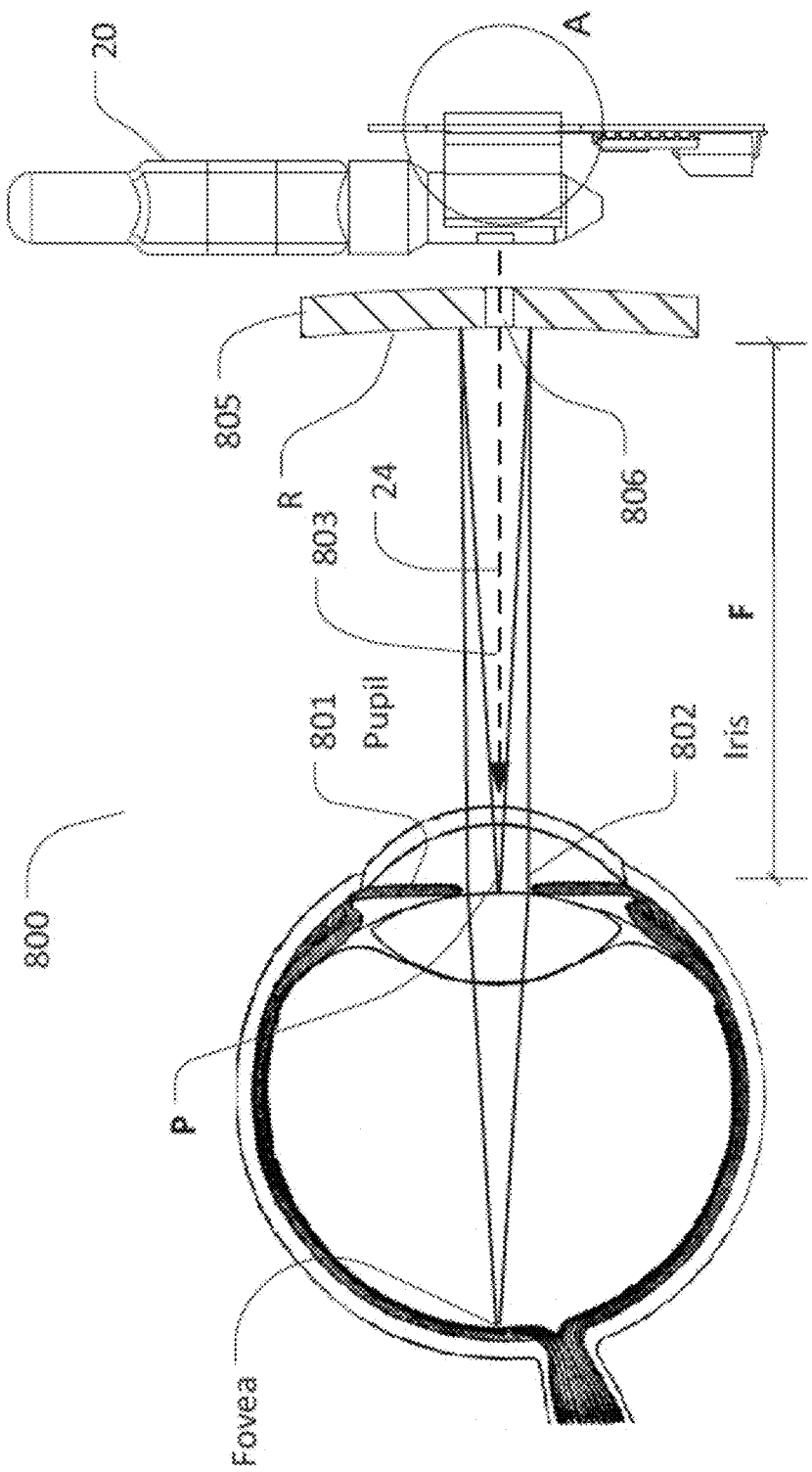
FIG. 4A illustrates an alignment system which facilitates aligning the fluid delivery assembly relative to the eye of the user when a reflected image of the eye appears in focus to the user.
Figure 4B:
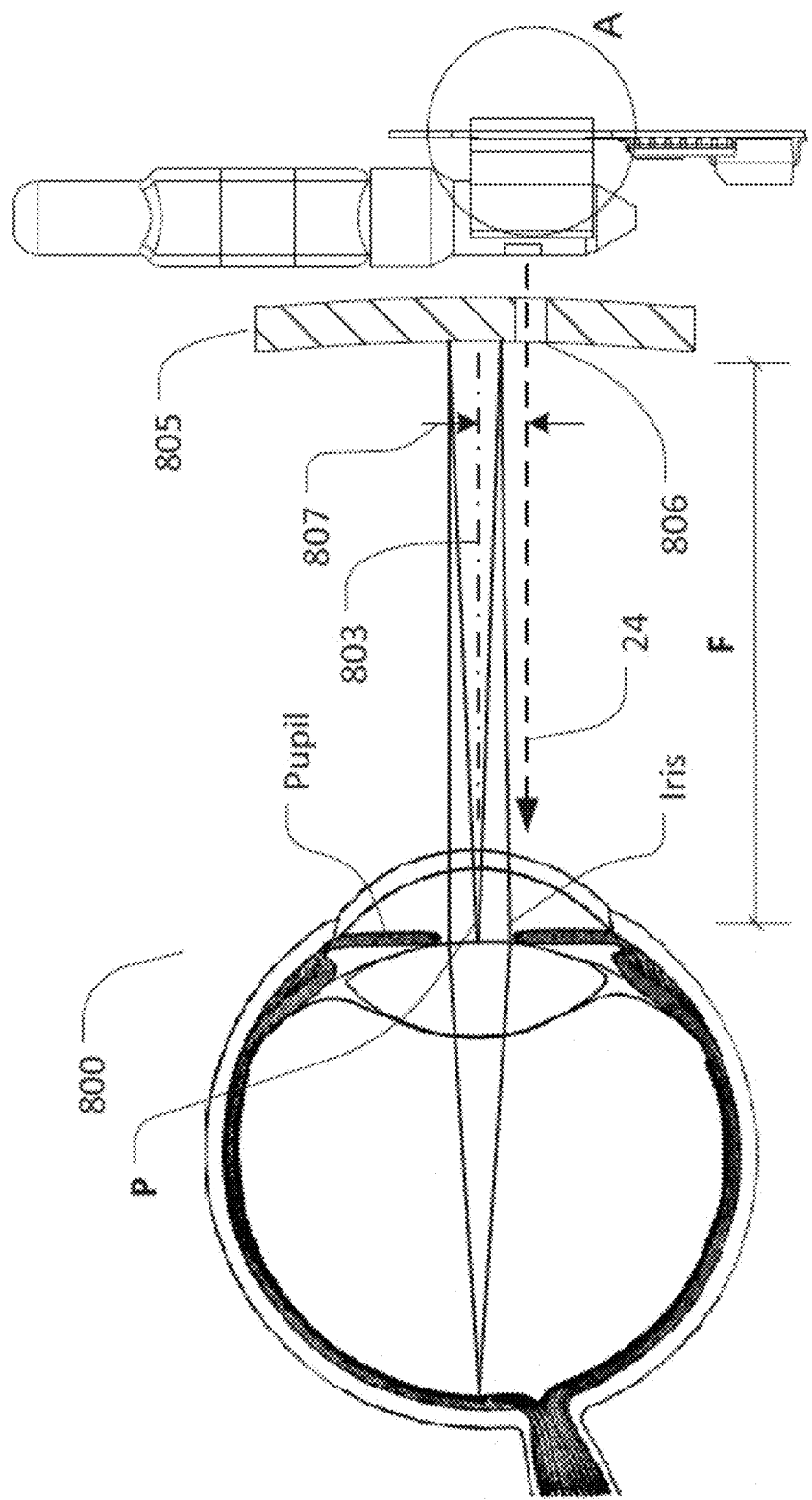
FIGS. 4B, 4C and 4D illustrate variations where the fluid is emitted off-axis or at an angle relative to a central visual axis of the iris.
Figure 4C:
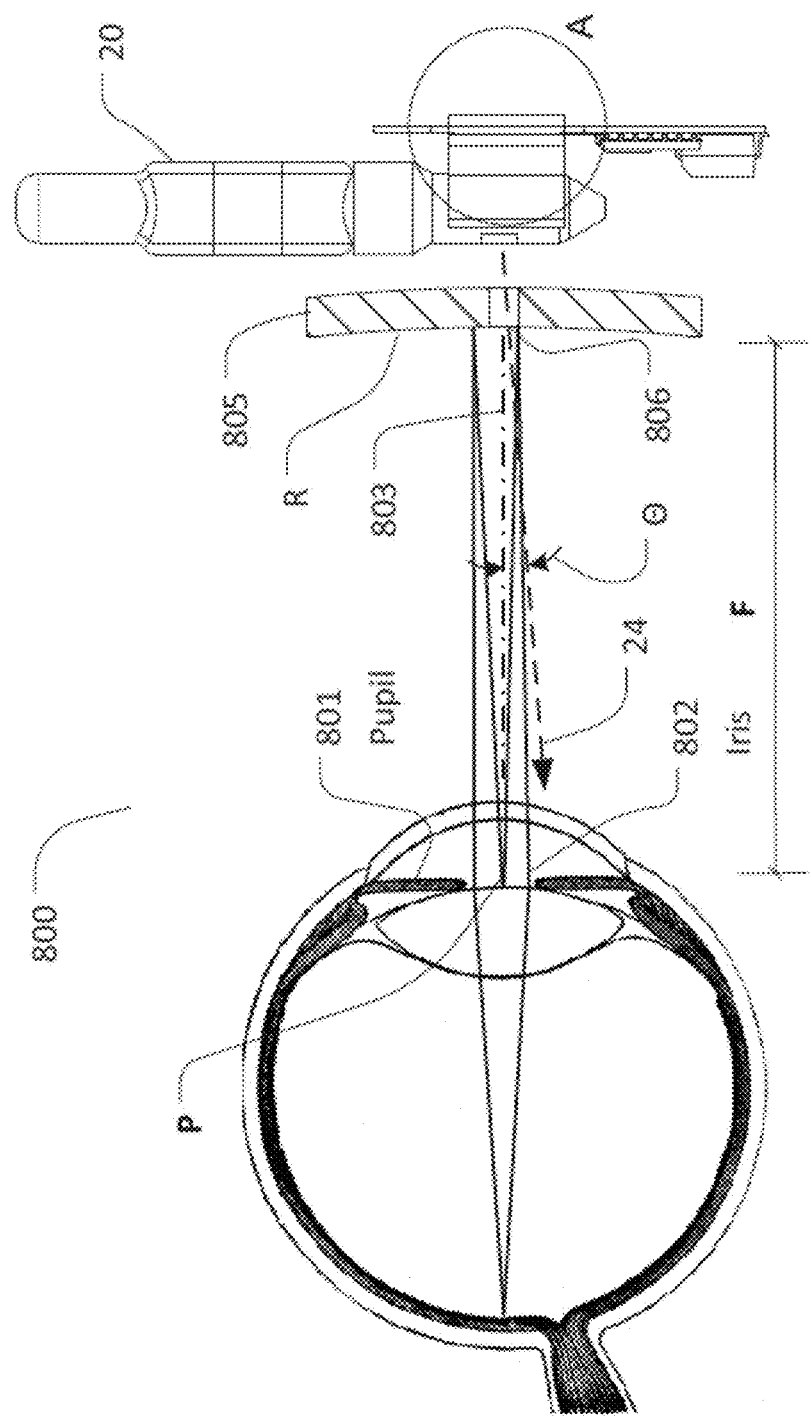
Figure 4D:
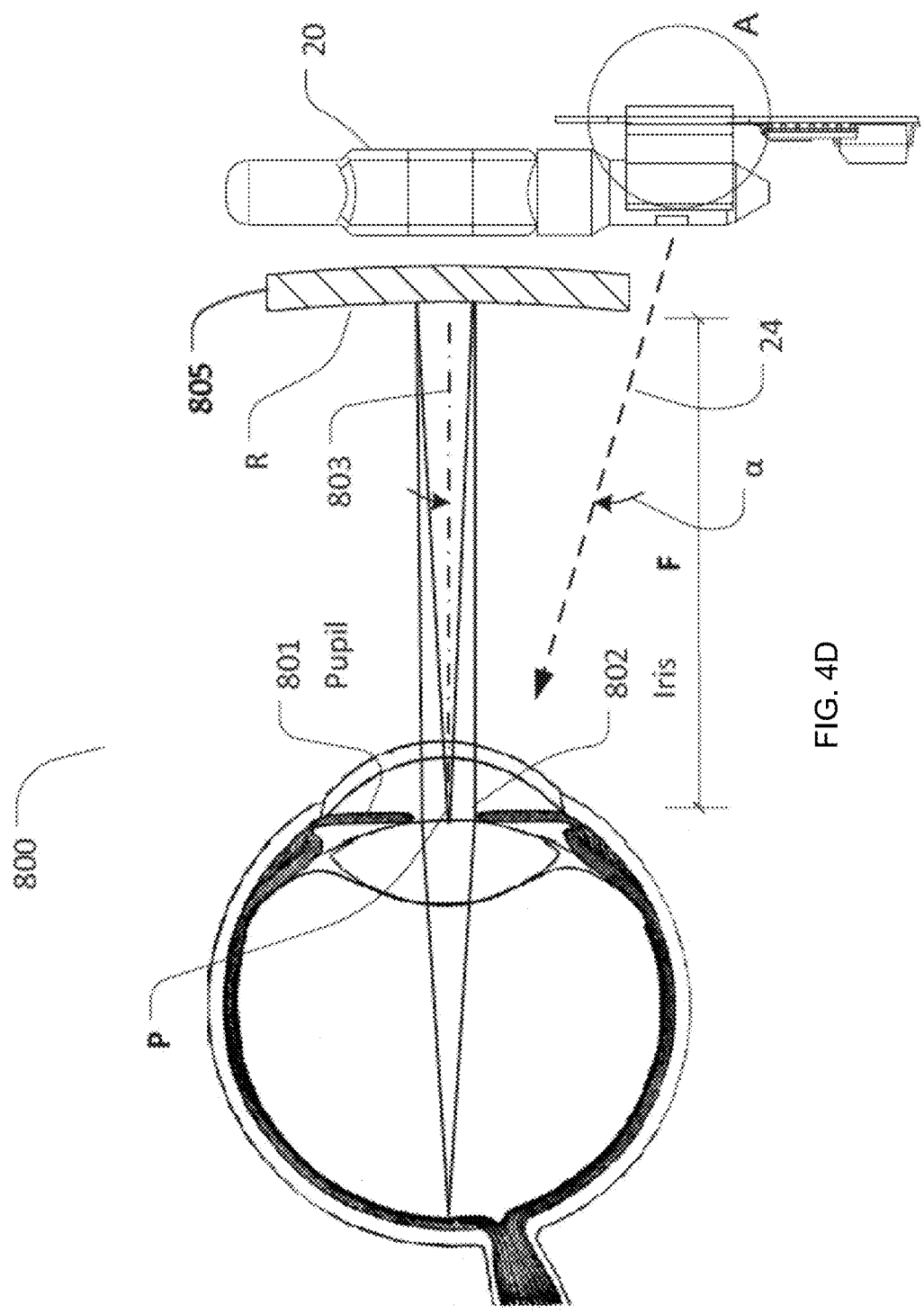

FIGS. 4A and 4B illustrate an alternative device and method for aligning the dispensing stream to the eye of the user. Referring to FIGS. 4A and 4B, it can be seen that dispensing device (800) includes a concave mirror (805), such as a spherical mirror having a radius of curvature (R), which defines the position of the focal point (P) at a focal distance (F) as F=R/2 from the mirror surface. The focal plane of the mirror is perpendicular to its optical axis and crosses it at the focal point (P). The mirror (805) may be spherical or aspherical in shape and may be fabricated using any number of materials and techniques. For instance, the mirror (805) may be manufactured from mirrored glass, reflective coatings overlaid upon a substrate, any number of reflective metals, etc. which facilitates removal or cleaning of any ejected fluid which may be deposited upon the mirror (805).

Mirror (805) is positioned in close proximity in front of dispensing ampule (20). Mirror (805) includes a small opening (806) which may be coaxially oriented relative to the stream (24), in one embodiment, for delivery fluid to the eye. While a single opening (806) is shown in this embodiment, multiple openings may be used or defined over the surface of the mirror (805) to accommodate one or more apertures for fluid ejection from the transducer assembly.

In use, the device (800) is aligned to the user eye such that the visible parts of the eye (e.g., cornea, iris, sclera, conjunctiva, etc.) are imaged onto the retina. For the image to be in focus, the mirror (805) should be positioned such that the tissue of interest, e.g., target ocular location, is in the focal plane (or near the focal plane) of the mirror (805). The eye tissue is clearly visible to the user in the reflection from the mirror (805) when the eye is located at the focal plane, e.g., when the distance from the mirror (805) to the tissue of interest, e.g., iris (802), is relatively close to the focal distance (F) of the mirror (805). Such an alignment method helps the user to properly align the dispensing device both in terms of the angle relative to the eye, its lateral position and in terms of setting the distance from the device to the eye. Both are accomplished when the user sees an image of his or her pupil of the eye that includes the target ocular location in the center of the mirror and when such image appears in focus. This alignment mechanism takes advantage of the mirror's natural focal distance and further provides for magnification of the reflected eye so that positioning of the eye relative to the assembly is facilitated, particularly for users whose eyesight may be degraded.

Figure 6:
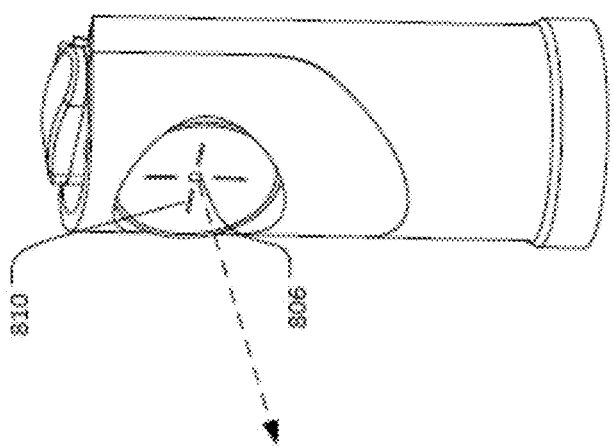
FIG. 6 illustrates a perspective view of the assembly.

As the radius of curvature of the mirror becomes smaller, the focal point becomes relatively closer to the eye, and the magnification of this imaging system becomes relatively higher. For instance, a flat mirror (one having an infinite radius of curvature) can provide an image only at the distance where the eye can naturally focus onto, which is typically more than about 30 cm from the eye. Due to the double passing of light from the object to the mirror and back to the eye, the minimal distance from the flat mirror to the eye will be about 15 cm. Holding a device so far from the eye will require precise angular alignment to ensure the proper targeting, and also requires the emitted fluid to propagate over a large distance without much divergence. Both of these requirements are hard to meet. Therefore, it is advantageous to use a concave mirror, which places the focal plane closer to the eye. The optimal distance ranges from at a short (first) end defined by the convenience of holding the device without touching the eye lashes, and at a long (second) end defined by the divergence of the emitted fluid, its deviation from the straight line and by the precision of the angular alignment by the user. The latter may be defined as a ratio of the allowable lateral displacement (misalignment) of the emitted fluid divided by the distance between the ejector and the targeted tissue. The closer the device is to the target tissue, the larger is the allowed angle of misalignment, where the emitted fluid will still hit the target area, i.e. the easier it will be for the users to hit the target. In one variation, the optimal range of the distances between the ejector and the targeted tissue (e.g., cornea) is in the range of, e.g., 10-100 mm, such as 20-100 mm, and including 30-60 mm.

As illustrated in FIG. 4A, emitting stream (24) may be coaxial and parallel with the principle axis (803) of the mirror (805) and/or with the central longitudinal axis of the iris (802) or in some offset from the central, visual axis of the iris (802) as illustrated in FIG. 4B. In this embodiment, the fluid ejected through the opening (806) may be emitted in a direction which is parallel relative to the principle axis or to the central longitudinal axis of the iris (802) so that the ejected fluid contacts the eye at a surface region offset from the central axis as well, e.g., cornea, conjunctiva. In yet another alternative shown in FIG. 4C, the ejected fluid (24) may be emitted from the opening (806) which may be centrally located, but the fluid may be emitted at an angle (Θ) relative to the principle axis of the eye (802).

In another variation, as shown in FIG. 4B, the aperture and opening (806) defined in the mirror (805) may be offset by a distance (807) relative to the principle axis (803). The opening (806) may be accordingly offset by the same distance from the axis (803). The ejected fluid (24) may be emitted towards the targeted region on the eye in a trajectory parallel with the principle axis (803).

In yet another variation, as shown in FIG. 4D, the mirror (805) may entirely omit the opening (806). The fluid delivery assembly may be positioned adjacent to the mirror (805) rather than located behind a proximal surface of the mirror (805), e.g., located behind the mirror (805) relative to the position of the eye when in use. Thus, the aperture of the fluid delivery assembly may be positioned, e.g., above, below, side, etc. relative to the mirror (805) so that the fluid may be emitted from the aperture at an angle (a) relative to the principle axis (803) and towards the targeted region on the surface of the eye.

In yet another variation, as shown in FIG. 4E, the alignment system may include a combination of a mirror (811) and a lens (812) as an alternative to a concave mirror. The mirror (811) may comprise a variety of various reflective materials or surfaces, e.g., a metallic layer, having a flat surface on its reflective side (813). The distal surface of the lens (812), which may also define a flat surface, may be positioned directly against the reflective surface (813) of the mirror (811) and both the mirror (811) and lens (812) may each define one or more openings (806) through which the fluid is delivered. The proximal surface of the lens may be convex (814), as shown. In other variations, fluid delivery assembly may be positioned relative to the mirror (811) and lens (812) assembly as described in other embodiments herein. In use, light may be refracted by the lens (812) and reflected from the mirror (811) in such a way that the front of the eye (iris (802) or conjunctiva or cornea) is imaged onto the retina. In this arrangement, light scattered from the eye passes twice through the lens (812) before and after reflection in the mirror (811).

Regardless of whether the fluid is ejected along the central axis (as shown in FIG. 4A) or offset or at an angle relative to the central axis (as shown in FIGS. 4B, 4C and 4D), the fluid may be emitted from any number of locations along the mirror (805), adjacent to the mirror (805), or emitted at any number of angles relative to the longitudinal axis of the iris (802) so that the fluid may be directed to contact the surface of the patient's eye at any number of predetermined locations. For instance, the fluid may come from multiple locations, or from multiple apertures from one or more locations over the same or different areas of the mirror, e.g., nasally and temporally at the same time. Additionally, multiple streams of fluid may be emitted simultaneously or serially, or both, if so desired.

In some instances, the optimal focal distance of the mirror (805) ranges, e.g., from 30 mm to 60 mm. Accordingly, in such instances the radius of curvature of the mirror ranges, e.g., from 60 mm to 120 mm, respectively. The diameter of the mirror may be selected such that the image of the iris is easily identified and the pupil is aligned to the center of the mirror. For this purpose, the diameter of the mirror may be slightly larger than a size of the iris and the size may range, e.g., from 15 mm to 30 mm. Alternatively, the diameter of the mirror may be selected so as to provide an image of only a portion of the eye, and in such instances may range from 11 to 15 mm, such as 13 mm.

As illustrated in FIGS. 5, 5A, 5B and FIG. 6, the mirror (805) may be part of the housing of the device and is made of transparent plastic such as polycarbonate and include a reflective metal layer.

As previously disclosed, the alignment mechanism takes advantage of the mirror's natural focal distance and further provides for magnification of the reflected eye so that positioning of the eye relative to the assembly is facilitated. Size of the image of the eye seen in reflection in the mirror is dependent on the radius of curvature of the mirror (805). The reflection of the eye appears larger to the user viewing the mirror (805) when the radius of curvature of the mirror (805) is smaller and vice versa. An example of this is shown in FIGS. 5A and 5B where the radius of curvature of the mirror (805) in FIG. 5A is, e.g., 60 mm, while the radius of curvature of the mirror in FIG. 5B is, e.g., 30 mm. Consequently, the size of the reflected image appears relatively larger in FIG. 5B. Accordingly, not only the size but the radius of curvature of the mirror may be varied depending upon the desired size of the reflected image.

The mirror (805) may be sized, in one embodiment, to have a circular shape when viewed by the patient so that the reflected image of the patient's eye or iris becomes framed within the mirror (805), as shown in FIGS. 5A and 5B. In other variations, the mirror may be configured to have other shapes when viewed, e.g., elliptical, square, triangular, etc. so long as the eye or iris is visible when properly positioned relative to the assembly. This may be implemented as an indicator to the user that the eye that includes the target location is suitably positioned relative to the opening (806) so that the ejected fluid may be suitably administered to the patient's eye. Additionally, the mirror (805) may also optionally include any configuration of markers or gradations (810), as shown in FIGS. 5A and 6, such as a target or reticle to further facilitate positioning of the patient's iris relative to the assembly. Although the markers or gradations (810) may not be visible to the user as the surface of the mirror may be out of focus, they may be optionally included to facilitate initial positioning relative to the user's eye.

Figure 7:
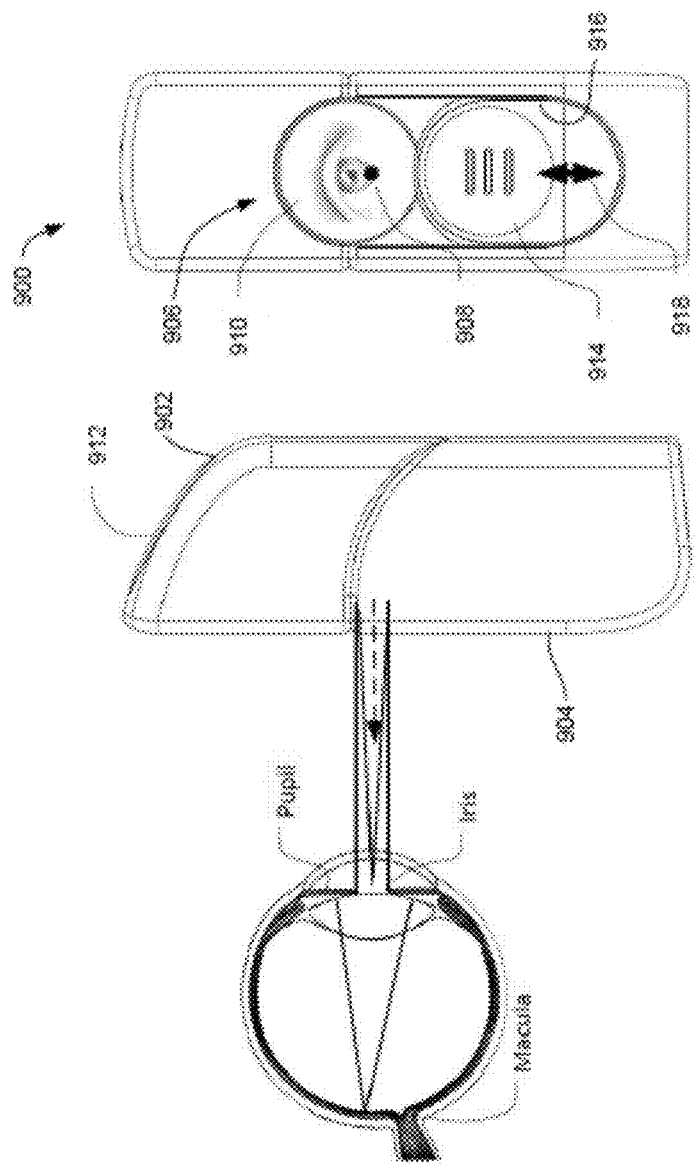
FIGS. 7A and 7B illustrate front and side views of an embodiment of the assembly having a protective covering feature.

In yet another embodiment, an example of a housing assembly (900) is shown in front and side views of FIGS. 7A and 7B, where a body of the housing (902) may incorporate one or more gripping surfaces (904) upon or around the housing (902). The assembly (900) has a form factor which facilitates the user holding and/or positioning the device relative to the tissue target of interest, such as one or both eyes, by enabling the user to comfortably hold and manipulate the device with a single hand. The housing assembly (900) may accordingly contain and/or enclose the various components of the actuator assembly (906) such as the piezoelectric actuator and actuator controller as well as the ampule, alignment assembly, etc.

With the gripping surfaces (904) thus defined, the one or more apertures through which the fluid is ejected may be positioned in alignment with an opening, slot, or slit (908) defined along the device through which the fluid may pass. Additionally, the assembly may incorporate any of the alignment mechanisms described. In this variation, the alignment mirror (910) is shown to illustrate how such a mechanism may be incorporated into the assembly where the mirror (910) defines the opening, slot, or slit (908) which is in proximity to the one or more apertures. The alignment mirror (910), or any of the other alignment mechanisms, may be incorporated into the assembly (900) and used to enable the user to self-align the one or more apertures to the targeted tissue region and administer fluid delivery for treatment.

As previously described, the size, orientation, and/or location of the one or more apertures may vary. Furthermore, multiple apertures and/or aperture geometries (such as a slit to create a "plane" of fluid) may be optionally incorporated.

The housing (902) may also incorporate an actuator (912), such as a button, switch, or other actuation mechanism to begin the dispensing of the fluid. The actuator (912) is illustrated in this embodiment as a button-type located atop the housing (902) so that the user may depress the actuator (912) during use; however, the actuator (912) may be positioned elsewhere along the housing (902). Additionally, and/or optionally, the aperture (908) may incorporate a shutter or other covering which may open or close when actuated such as by activating the actuator (912).

Another component of the housing assembly (900) may include a cover element (914) which may be moved between a closed and opened position, as indicated by the direction of movement (918). In its closed position, the cover (914) may partially or completely cover or obstruct the alignment mechanism and aperture as well as optionally deactivate the assembly so that fluid is prevented from being dispensed. In its open position, the alignment mechanism and aperture may be unobstructed for use and the assembly may be activated or powered on for dispensing the fluid.

In this variation, the cover element (914) is configured as a sliding cover which may be translated within a channel or groove (916). Sliding the cover into its open position, as shown, exposes the mirror (910), the opening (908) and one or more apertures, and may also power the device on. Sliding the cover into its closed position may slide the cover over the mirror (910), opening (908), and may further deactivate the assembly. While the cover is shown as a sliding mechanism, other variations may incorporate a rotating cover or a cover which may be removed entirely as a separate or coupled structure. Additionally, during use, the cover element (914) may also serve as a thumb-rest, such that the patient uses his/her own thumb as a brace against his/her cheek to stabilize and align the device during use.

Figure 8:
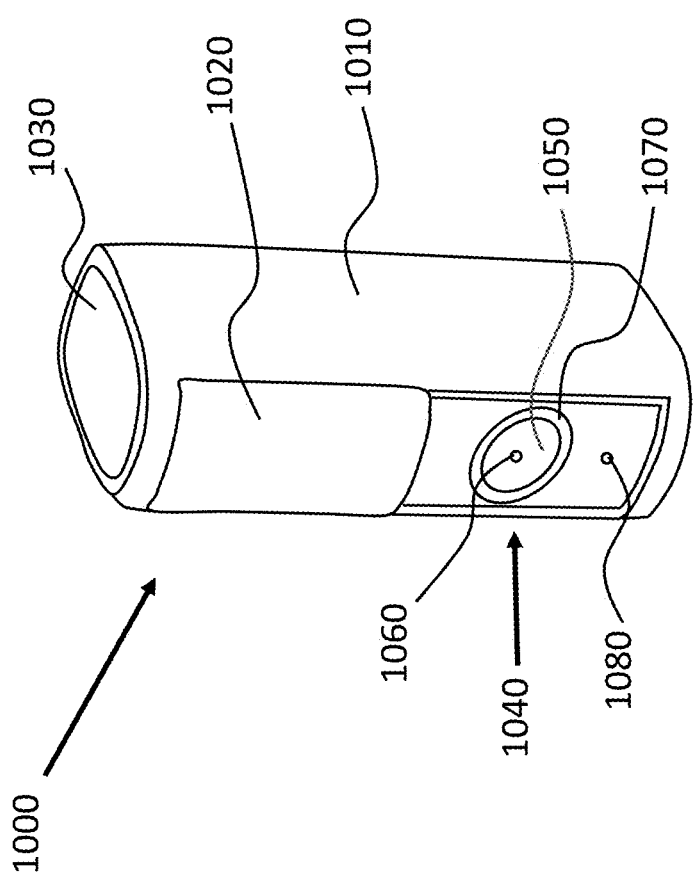
FIG. 8 illustrates another embodiment of a fluid delivery device having a ring LED around a concave mirror and an IR distance sensor.

FIG. 8 provides a view of another embodiment of a fluid delivery device in accordance with the invention. As shown in FIG. 8, device (1000) includes a housing (1010) having a sliding cover (1020). Present in the housing a fluid delivery package and actuator, e.g., as described above. As shown, the device (1000) includes an actuator button (1030) on the top of the housing. The device also includes a concave-mirror image-based alignment system (1040) as described above, where the concave mirror (1050) includes an opening (1060) through which fluid ejected from the aperture may flow during fluid delivery. Surrounding or bounding the concave mirror (1050) is circular LED (1070). Also shown is IR sensor (1080).

Methods

As summarized above, aspects of the present disclosure include methods of administering an active agent to a target location, such as an ocular location, of a subject. By target ocular location is meant a region (i.e., area or domain) of an eye surface, such a region of a cornea, a region of a conjunctiva, a region that includes both corneal and conjunctival components, etc. In some instances, the target ocular location is an area or region that is offset relative to the optical axis of the eye. In some instances, the target location is on either the bulbar or tarsal conjunctiva, or in the conjunctival fornix. In other words, the target topical ocular location is one that is displaced from the center of the pupil or the center of the iris. While the magnitude of the distance of the offset/displacement may vary, in some instances the magnitude ranges from 1 to 20 mm, such as 2 to 20 mm, e.g., 5 to 15 mm, including 5 to 10 mm. While the target topical ocular location may vary in size, in some instances the size of the target topical ocular region is 15 mm$^2$ or less, ranging in some instances from 1 to 15 mm$^2$, such as from 2.5 to 12 mm$^2$, including from 3 to 9 mm$^2$.

Aspects of embodiments of the methods include delivering to the target location a dosage of a liquid formulation of the active agent. In some instances, the delivered dosage is a dosage having a volume that can be wholly accommodated by the tear film of the target topical ocular location. The tear film of the target topical ocular location is the film that is associated with the target topical ocular location. As such, the tear film is the film or layer of tear liquid that is present on the eye surface on which the target topical ocular location, e.g., as described above, is located. As the delivered dosage has a volume that may be wholly accommodated by the tear film of the target topical ocular location, it may also be a volume that may be wholly accommodated by the ocular surface that includes the target topical ocular location. By "wholly accommodated by the ocular surface" is meant that, upon delivery, the delivered dosage has a volume that can be held on the surface of the eye to which it is administered without any excess liquid running off of the surface of the eye and over the eyelid, e.g., in the form of tears. While the volume of a given delivered dosage may vary, in some instances the volume ranges from 1 to 15 µl, such as 5 to 10 µl.

In some instances, the delivered dosage is one that has an efficacy comparable to a reference dosage having a volume that exceeds the capacity of the tear film of the target topical ocular location. The reference dosage in such instances, apart from volume, is otherwise identical to that of the delivered dosage. As such, the concentration of the active agent in the reference dosage is the same as the concentration of the active agent in the delivered dosage. The volume of the reference dosage exceeds that of the delivered dosage, e.g., by 2 fold or greater, such as 3 fold or greater. In some instances, the reference dosage has a volume ranging from 25 to 60 µl, such as 30 to 50 µl. In some instances, the reference dosage is a dosage that is delivered by a standard eye dropper device.

The delivered dosage of the liquid formulation of the active agent may be administered to the target topical ocular location as a stream, where the stream may be a continuous stream of liquid (i.e., a stream that is not made up of individual droplets) or a discontinuous stream of liquid, e.g., a collimated stream of individual droplets, or include both continuous and discontinuous components. Where the stream is a continuous stream of liquid, the stream diameter may vary, and in some instances ranges from 0.05 to 0.15 mm, such as 0.070 to 0.130 mm. Where the stream is a discontinuous stream of individual droplets, the volume of the individual droplets may vary, ranging in some instances from 50 to 1500 µl, such as 100 to 1000 µl. The velocity of the stream may vary, ranging in some instances from a value generally above the minimum exit velocity of the fluid from the aperture. The minimum exit velocity is defined in a scientific article titled "Production of uniform-size liquid droplets" N. R. Lindblad and J. M Scheider equation 2. This article is incorporated herein by reference. In some instances, the exit velocity is 20% or more above the minimum exit velocity and in some instances is 300% or less above the minimum exit velocity. For example, for an aperture size of 125 micron the minimum velocity is 194 cm/sec but the selected velocity would at least 30% higher i.e., 252 cm/sec. The duration of stream delivery during a given administration event may vary and is selected so as to provide the desired delivered dosage volume, e.g., as described above. Ideally, duration of stream delivery should be below the blink response time, i.e., below 150 ms. If necessary, the duration of administration could be extend for 250 ms or even up to 1000 msec. In some instances the duration is 100 ms or longer.

The delivered dosage may be administered to the target topical ocular location using any convenient protocol. In some instances, the delivered dosage is administered to the target topical ocular location by an individual other than the subject, e.g., where the delivered dosage is administered by a health care professional, such as a physician or nurse. In other instances, the delivered dosage is self-administered by the subject, e.g., where the subject administers the dosage to a target topical ocular location of one of the subject's own eyes.

Methods of the invention may include aligning the device with the target location. Where the target location is an eye of the user, e.g., where the device is employed for self-administration, the methods may include the user aligning the device with the target location using the eye that includes the target location, e.g., as described above, such that the same eye that has the target location is used to align the device with the target location.

As summarized above, the delivered dosage is a volume of a liquid formulation of an active agent. The terms "agent," "compound," and "drug" are used interchangeably herein to refer to a molecule or molecular combination that has a physiological effect upon contact with a subject via administration to the target topical ocular location of the subject. Examples of active agents that may be present in the liquid formulation include, but are not limited to: anti-infectives (including but not limited to antibiotics, antivirals, etc.), anti-inflammatories (including but not limited to steroids and non-steroidal anti-inflammatory drugs (NSAIDS), etc.), anti-allergy agents (including but not limited to anti-histamines and mast cell stabilizers, etc.), anti-fungals, vasoconstrictors, biologics (e.g. proteins, engineered proteins, etc.), small molecules, anesthetics, analgesics, intraocular pressure lowering agents (including but not limited to prostaglandin analogs, ROK inhibitors, beta blockers, carbonic anhydrase inhibitors, and alpha agonists, etc.), lubricants (including but not limited to saline, polymer solutions, proteoglycans, glycosaminoglycans, carbohydrates, etc.), mydriatic (pupil dilating) agents, miotic agents (pupil constricting agents), iodine derivatives, etc.; and/or various combinations thereof. Additional drugs and agents which may be utilized with the devices described may include any number of the agents disclosed in further detail in U.S. Pub. 2017/0344714 and U.S. Pat. No. 9,087,145 the disclosures of which are herein incorporated by reference.

In some embodiments, the concentration of active agent in the liquid formulation ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In addition to the active agent, the liquid formulation may include an aqueous delivery vehicle, e.g., a pharmaceutically acceptable aqueous vehicle. In addition to water the aqueous delivery vehicle may include a number of different components, including but not limited to: salts, buffers, preservatives, solubility enhancers, viscosity modulators, colorants, etc. Suitable aqueous vehicles include sterile distilled or purified water, isotonic solutions such as isotonic sodium chloride or boric acid solutions, phosphate buffered saline (PBS), propylene glycol and butylene glycol. Other suitable vehicular constituents include phenylmercuric nitrate, sodium sulfate, sodium sulfite, sodium phosphate and monosodium phosphate. Additional examples of other suitable vehicle ingredients include alcohols, fats and oils, polymers, surfactants, fatty acids, silicone oils, humectants, moisturizers, viscosity modifiers, emulsifiers and stabilizers. The compositions may also contain auxiliary substances, i.e. antimicrobial agents such as chlorobutanol, parabans or organic mercurial compounds; pH adjusting agents such as sodium hydroxide, hydrochloric acid or sulfuric acid; and viscosity increasing agents such as methylcellulose. An exemplary final composition is sterile, essentially free of foreign particles, and has a pH that allows for patient comfort and acceptability balanced with a pH that is desirable for optimum drug stability. An exemplary "pharmaceutically acceptable vehicle is an "ophthalmically acceptable vehicle" as used herein refers to any substance or combination of substances which are non-reactive with the compounds and suitable for administration to patient. In an exemplary embodiment, the vehicle is an aqueous vehicle suitable for topical application to the patient's eyes. In various embodiments, the vehicle further includes other ingredients which may be desirable to use in the ophthalmic compositions of the present invention include antimicrobials, preservatives, co-solvents, surfactants and viscosity building agents.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

In some aspects of the subject methods, the method further comprises the step of measuring efficacy of a given condition, e.g., of a disease condition in the subject. In some such instances, the determination is made by comparing the results to the results performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more. The evaluation may vary depending on the nature of the condition being treated. In some embodiments, the subject methods further include diagnosing an individual as having a given condition.

The above methods find use in a variety of different applications. Certain applications are reviewed in greater detail in the Utility section, below.

Utility

The subject devices and methods find use in a variety of different applications, including both treatment and diagnostic/examination applications. The term "treating" or "treatment" as used herein means the treating or treatment of a disease or medical condition in a subject or patient, such as a mammal (such as a human), where the term includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

An example of a condition that may be treated using methods/devices of the invention is glaucoma. Glaucoma is a collection of disorders characterized by progressive visual field loss due to optic nerve damage. It is the leading cause of blindness in the United States, affecting 1-2% of individuals aged 60 and over. Although there are many risk factors associated with the development of glaucoma (age, race, myopia, family history, and injury), elevated intraocular pressure, also known as ocular hypertension, is the only risk factor successfully manipulated and correlated with the reduction of glaucomatous optic neuropathy. In glaucoma associated with an elevation in eye pressure the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The aqueous or aqueous humor is a transparent liquid that fills the region between the cornea at the front of the eye and the lens. The aqueous humor is constantly secreted by the ciliary body around the lens, so there is a continuous flow of the aqueous humor from the ciliary body to the eye's front chamber. The eye's pressure is determined by a balance between the production of aqueous and its exit through the trabecular meshwork (major route) or via uveal scleral outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanilicular meshwork).

In embodiments where the methods and devices are used in treating glaucoma, the delivered dosage may include an intraocular pressure modulatory agent. An "intraocular pressure modulatory agent" can comprise a drug and may be any of the following or their equivalents, derivatives or analogs, including anti-glaucoma medications (e.g. adrenergic agonists, adrenergic antagonists (beta blockers), carbonic anhydrase inhibitors (CAIs, systemic and topical), therapeutic agent(s) such as prostaglandins, prostaglandin precursors, including antiglaucoma drugs including beta-blockers such as timolol, betaxolol, levobunolol, atenolol (e.g., as described in U.S. Pat. No. 4,952,581); adrenergic agonists including clonidine derivatives, such as apraclonidine or brimonidine (e.g., as described in U.S. Pat. No. 5,811,443); and prostaglandin analogues such as bimatoprost, travoprost, tafluprost, latanoprost, etc. In some instances, the therapeutic agent is already marketed for glaucoma, and commercially available preparations thereof can be used. Further therapeutic agents include carbonic anhydrase inhibitors such as acetazolamide, dorzolamide, brinzolamide, methazolamide, dichlorphenamide, diamox; and the like.

Other disease conditions that may be treated by methods and devices of the invention include, but are not limited to, those described in U.S. Pub. 2017/0344714 and U.S. Pat. No. 9,087,145 the disclosures of which are herein incorporated by reference.

Diagnostic/examination applications include, but are not limited to, mydriasis applications where the pupil is dilated, e.g., to permit examination of the retina and other deep structures of the eye. Mydriatic agents that may be employed in such applications include, but are not limited to: atropine, atropine sulfate, atropine hydrochloride, atropine methylbromide, atropine methylnitrate, atropine hyperduric, atropine N-oxide, phenylephrine, phenylephrine hydrochloride, hydroxyamphetamine, hydroxyamphetamine hydrobromide, hydroxyamphetamine hydrochloride, hydroxyamphetamine iodide, cyclopentolate, cyclopentolate hydrochloride, homatropine, homatropine hydrobromide, homatropine hydrochloride, homatropine methylbromide, scopolamine, scopolamine hydrobromide, scopolamine hydrochloride, scopolamine methylbromide, scopolamine methylnitrate, scopolamine N-oxide, tropicamide, tropicamide hydrobromide, and tropicamide hydrochloride.

Kits

Also provided are kits that find use in practicing embodiments of the methods, such as those described as described above. The term "kit" refers to a packaged delivery device or component thereof, e.g., ampule, such as described above. In addition to the above-mentioned components, kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Notwithstanding the appended claims, the disclosure set forth herein is also defined by the following clauses:

1. A fluid delivery device, the device comprising:
   (a) a fluid package comprising a reservoir comprising a fluid and one or more apertures; and
   (b) an actuator configured to eject fluid from the reservoir through the one or more apertures; and
   (c) an image-based alignment system configured to align fluid ejected through the one or more apertures with a target location.
2. The fluid delivery device according to Clause 1, wherein the fluid comprises an ophthalmic fluid and the target location is an ocular location.
3. The fluid delivery device according to Clauses 1 or 2, wherein the fluid package is disposable.
4. The fluid delivery device according to any of the preceding clauses, wherein the actuator is configured to produce cycles of acoustic pressure in the fluid so as to eject fluid from the reservoir through the one or more apertures.
5. The fluid delivery device according to any of the preceding clauses, wherein the actuator comprises a piezoelectric actuator.
6. The fluid delivery device according to any of the preceding clauses, wherein the actuator component is reusable.
7. The fluid delivery device according to any of the preceding clauses, wherein the image-based alignment system comprises a reflective surface.
8. The fluid delivery device according to Clause 7, wherein the reflective surface is curved.
9. The fluid delivery device according to Clause 8, wherein the reflective surface comprises a concave mirror.
10. The fluid delivery device according to Clause 9, wherein the concave mirror comprises a spherical or aspherical mirror.
11. The fluid delivery device according to Clause 7, wherein the reflective surface comprises a flat mirror.
12. The fluid delivery device according to Clause 11, wherein the alignment system comprises a lens positioned in front of the flat mirror.
13. The fluid delivery device according to Clause 12, wherein the lens has a convex surface.
14. The fluid delivery device according to any of Clauses 7 to 13, wherein the reflective surface has a longest dimension ranging from 10 to 30 mm.
15. The fluid delivery device according to Clause 14, wherein the reflective surface as a circular shape.
16. The fluid deliver device according to Clause 15, wherein the reflective surface has a diameter ranging from 10 to 15 mm.
17. The fluid delivery device according to any of Clauses 7 to 16, wherein the device is configured to eject the fluid co-axially with a principal axis of the reflective surface.
18. The fluid delivery device according to any of Clauses 7 to 16, wherein the device is configured to eject the fluid off-axis with a principal axis of the reflective surface.
19. The fluid delivery device according to Clause 18, wherein the device is configured to eject the fluid parallel to the principal axis.
20. The fluid delivery device according to Clause 18, wherein the device is configured to eject the fluid at an angle relative to a principal axis.
21. The fluid delivery device according to any of Clauses 1 to 6, wherein the image-based alignment system comprises a lenticular print.
22. The fluid delivery device according to Clause 21, wherein the lenticular print comprises an image and a focusing element overlaying the image.
23. The fluid delivery device according to Clause 22, wherein the focusing element comprises an array of linear lenses.
24. The fluid delivery device according to any of Clauses 21 to 23, wherein the alignment system comprises a more than one lenticular print.
25. The fluid delivery device according to any of the preceding clauses, wherein the fluid package and actuator component are present in a housing.
26. The fluid delivery device according to Clause 25, where the housing comprises a cover positioned along the housing, wherein the cover is configurable between an open position, in which the one or more apertures are exposed, and a closed position, in which the one or more apertures are not exposed.
27. The fluid delivery device according to Clause 26, wherein the cover comprises a sliding cover structure.
28. The fluid delivery device according to Clauses 26 or 27, wherein the actuator component is configured to be activated when the cover is in the open position.
29. The fluid delivery device according to any of Clauses 26 to 28, wherein the actuator component is configured to be deactivated when the cover is in the closed position.
30. The fluid delivery device according to any of the preceding clauses, wherein the device comprises an illumination source.
31. The fluid delivery device according to Clause 30, wherein the illumination source comprises an LED.
32. The fluid delivery device according to Clauses 30 or 31, wherein the illumination source is associated with the alignment system.
33. The fluid delivery device according to Clause 32, wherein the illumination source at least partially bounds the alignment system.
34. The fluid delivery device according to Clause 30 or 31, wherein the illumination source is distinct from the alignment system.
35. The fluid delivery device according to any of the preceding clauses, wherein the device further comprises a distance sensor configured to determine the distance between the device and the target location.
36. The fluid delivery device according to Clause 35, wherein the distance sensor comprises an infrared sensor.

37. The fluid delivery device according to Clause 35 or 36, wherein the device is configured to provide a signal when the determined distance between the device and the target location is within a predetermined range.

38. The fluid delivery device according to Clause 37, wherein the signal comprises an auditory signal or a visual signal.

39. The fluid delivery device according to any of Clauses 35 to 38, wherein the device is configured to be activated when the determined distance between the device and the target location is within a predetermined range.

40. The fluid delivery according to any of Clauses 37 to 39, wherein the predetermined range is from 10 to 100 mm.

41. A method of delivering a fluid to a target site of a subject, the method comprising:
(A) aligning a fluid delivery device with the target site, wherein the fluid delivery device comprises:
 (1) a fluid package comprising a reservoir comprising a fluid and one or more apertures; and
 (2) an actuator configured to eject fluid from the reservoir through the one or more apertures; and
 (3) an image-based alignment system configured to align fluid ejected through the one or more apertures with a target location
(B) activating the actuator to eject fluid from the reservoir through the one or more apertures to the target location.

42. The method according to Clause 41, wherein the fluid comprises an ophthalmic fluid.

43. The method according to Clauses 41 or 42, wherein the fluid package is disposable.

44. The method according to any of the preceding clauses, wherein the actuator is configured to produce cycles of acoustic pressure in the fluid so as to eject fluid from the reservoir through the one or more apertures.

45. The method according to any of Clauses 41 to 44, wherein the actuator comprises a piezoelectric actuator.

46. The method according to any of the preceding clauses, wherein the actuator component is reusable.

47. The method according to any of the preceding clauses, wherein the image-based alignment system comprises a reflective surface.

48. The method according to Clause 47, wherein the reflective surface if curved.

49. The method according to Clause 48, wherein the reflective surface comprises a concave mirror.

50. The method according to Clause 49, wherein the concave mirror comprises a spherical or aspherical mirror.

51. The method according to Clause 47, wherein the reflective surface comprises a flat mirror.

52. The method according to Clause 51, wherein the alignment system comprises a lens positioned in front of the flat mirror.

53. The method according to Clause 52, wherein the lens has a convex surface.

54. The method according to any of Clauses 47 to 53, wherein the reflective surface has a longest dimension ranging from 10 to 30 mm.

55. The method according to Clause 54, wherein the reflective surface as a circular shape.

56. The method according to Clause 55, wherein the reflective surface has a diameter ranging from 10 to 15 mm.

57. The method according to any of Clauses 47 to 56, wherein the device is configured to eject the fluid co-linearly with a principal axis of the reflective surface.

58. The method according to any of Clauses 47 to 56, wherein the device is configured to eject the fluid off-axis with a principal axis of the reflective surface.

59. The method according to Clause 58, wherein the device is configured to eject the fluid parallel to the principal axis.

60. The method according to Clause 58, wherein the device is configured to eject the fluid at an angle relative to a principal axis.

61. The method according to any of Clauses 41 to 46, wherein the image-based alignment system comprises a lenticular print.

62. The method according to Clause 61, wherein the lenticular print comprises an image and a focusing element overlaying the image.

63. The method according to Clause 62, wherein the focusing element comprises an array of linear lenses.

64. The method according to any of Clauses 61 to 63, wherein the alignment system comprises a more than one lenticular print.

65. The method according to any of Clauses 47 to 64, wherein the fluid package and actuator component are present in a housing.

66. The method according to Clause 65, where the housing comprises a cover positioned along the housing, wherein the cover is configurable between an open position, in which the one or more apertures are exposed, and a closed position, in which the one or more apertures are not exposed.

67. The method according to Clause 66, wherein the cover comprises a sliding cover structure.

68. The method according to Clauses 66 or 67, wherein the actuator component is configured to be activated when the cover is in the open position.

69. The method according to any of Clauses 66 to 68, wherein the actuator component is configured to be deactivated when the cover is in the closed position.

70. The method according to any of Clauses 66 to 69, wherein the method comprises moving the cover between the closed and open positions.

71. The method according to any of Clauses 41 to 70, wherein the device comprises an illumination source.

72. The method according to Clause 71, wherein the illumination source comprises an LED.

73. The method according to Clause 71 or 72, wherein the illumination source is associated with the alignment system.

74. The method according to Clause 73, wherein the illumination source at least partially bounds the alignment system.

75. The method according to Clause 71 or 72, wherein the illumination source is distinct from the alignment system.

76. The method according to any of Clauses 41 to 75, wherein the device further comprises a distance sensor configured to determine the distance between the device and the target location.

77. The method according to Clause 76, wherein the distance sensor comprises an infrared sensor.

78. The method according to Clause 76 or 77, wherein the device is configured to provide a signal when the determined distance between the device and the target location is within a predetermined range.

79. The method according to Clause 78, wherein the signal comprises an auditory signal or a visual signal.

80. The method according to any of Clauses 76 to 79, wherein the device is configured to be activated when the determined distance between the device and the target location is within a predetermined range.

81. The method according to any of Clauses 76 to 80, wherein the predetermined range is from 10 to 100 mm.

82. The method according to any of Clauses 41 to 81, wherein the target location is an ocular location.

83. The method according to Clause 82, wherein the ocular location comprises a corneal/conjunctival location.

84. The method according to Clause 83, wherein the ocular location comprises an area ranging from 2.5 to 12 µm².

85. The method according to any of Clauses 41 to 84, wherein the method is performed by the subject.

86. A kit comprising a fluid delivery device according to any of Clauses 1 to 40 or a component thereof.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

The invention claimed is:

1. A device for self-administration of a fluid to a target location, the device comprising:

a) a fluid delivery package having a reservoir including one or more apertures;
b) an actuator positioned adjacent the reservoir to act on the reservoir to eject fluid therefrom through the one or more apertures, the fluid being ejected towards the target location with a delivery time less than 150 ms; and
c) a concave mirror disposed downstream of the one or more apertures and having an opening through which the fluid ejected from the one or more apertures is directed, the concave mirror provided with a design to enable self-alignment of the device with the target location when an image of the target location is in focus and is centered in the concave mirror,
wherein the device further includes a housing, wherein the housing comprises a cover, and wherein the cover is configurable between an open position, in which the one or more apertures are exposed, and a closed position, in which the one or more apertures are not exposed, and wherein movement of the cover from the closed to the open position transitions the actuator from an inactive to active state.

2. The device according to claim 1, where the concave mirror is spherical.

3. The device according to claim 2, where the spherical mirror has a focal distance ranging from 10 to 100 mm.

4. The device according to claim 1, wherein the device comprises a light source for illumination of the target location.

5. The device according to claim 1, wherein the device further comprises a distance sensor configured to determine a distance between the device and the target location.

6. The device according to claim 5, wherein the device is configured to provide a signal when the determined distance between the device and the target location is with a predetermined range.

7. The device according to claim 1, wherein the one or more apertures are disposed at corresponding offsets relative to an optical axis of the concave mirror, and wherein the offsets are in a range from 1 mm to 20 mm.

8. The device according to claim 1, wherein the device further includes a switch configured to control the actuator.

9. The device according to claim 1, wherein the concave mirror is further configured to enable the self-alignment of the device by transitioning a blurry image, as viewed from an eye of a user, into an in-focus image in the concave mirror signifying to the user that the device is properly aligned.

10. The device according to claim 1, wherein the concave mirror magnifies the image in the concave mirror to facilitate the self-alignment of the device.

* * * * *